United States Patent
Taylor et al.

(10) Patent No.: US 9,834,756 B2
(45) Date of Patent: Dec. 5, 2017

(54) METHODS FOR INCREASING ISOLATION YIELDS OF CELLULAR PRODUCTS

(75) Inventors: Michael J. Taylor, Mt. Pleasant, SC (US); Simona C. Baicu, Charleston, SC (US); David Kravitz, Barrington Hills, IL (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 653 days.

(21) Appl. No.: 13/183,961

(22) Filed: Jul. 15, 2011

(65) Prior Publication Data

US 2012/0015343 A1    Jan. 19, 2012

Related U.S. Application Data

(60) Provisional application No. 61/365,103, filed on Jul. 16, 2010.

(51) Int. Cl.
*C12N 5/071* (2010.01)
*A01N 1/02* (2006.01)

(52) U.S. Cl.
CPC ......... *C12N 5/0676* (2013.01); *A01N 1/0247* (2013.01)

(58) Field of Classification Search
None
See application file for complete search history.

(56) References Cited

U.S. PATENT DOCUMENTS

| | | | |
|---|---|---|---|
| 5,405,742 A | 4/1995 | Taylor | |
| 5,514,536 A | 5/1996 | Taylor | |
| 5,599,659 A | 2/1997 | Brasile et al. | |
| 5,643,712 A | 7/1997 | Brasile | |
| 5,699,793 A | 12/1997 | Brasile | |
| 5,702,881 A | 12/1997 | Brasile et al. | |
| 5,723,282 A | 3/1998 | Fahy et al. | |
| 5,843,024 A | 12/1998 | Brasile | |
| 6,492,103 B1 * | 12/2002 | Taylor | A01N 1/02 435/1.2 |
| 6,994,954 B2 | 2/2006 | Taylor | |
| 7,504,201 B2 | 3/2009 | Taylor et al. | |
| 2005/0255442 A1* | 11/2005 | Brassil | A01N 1/02 435/1.2 |

OTHER PUBLICATIONS

2004 KPS1 solution brochure.*
Hosgood et al. (Transplantation, vol. 89, No. 10, pp. 1169-1175; published May 27, 2010).*
Hosgood et al. (Transplantation, vol. 89, No. 1 O, pp. 1169-1175; published May 27, 2010) (of record).*
Taylor et al., Transplantation Proceedings, vol. 40, pp. 480-482; 2008 (of record).*
Taylor et al., Cell Transplantation, vol. 19, pp. 613-628; Jan. 20, 2010 (of record).*
Baicu et al., Clinical Transplantation, vol. 18, Supplement 12, pp. 16-21; 2004 (of record).*
2004 KPS1 solution brochure (of record).*
Jan. 22, 2013 International Preliminary Report on Patentability issued in PCT/US2011/044210.
Baicu, Simona C et al., "Interstitial fluid analysis for assessment of organ function", Clinical Transplantation. 18, Suppl. 12:16-21; 2004.
Taylor, Michael J., et al., "Hypothermic perfusion of pancreas: Emphasis on preservation prior to islet isolation", 2009, pp. 1-43, Artech House Publisher, Boston, USA.
Taylor, Michael J. et al., "Current state of hypothermic machine perfusion preservation of organs: The clinical perspective", Cryobiology, pp. 1-16, 2009, Elsevier, Inc., USA.
Taylor, Michael J. et al., "Islet Isolation From Juvenile Porcine Pancreas After 24-h Hypothermic Machine Perfusion Preservation", 2010, pp. 1-16, Cell Transplantation, vol. 19.
Taylor, Michael J. et al., "Twenty-Four Hypothermic Machine Perfusion Preservation of Porcine Pancreas Facilities Processing for Islet Isolation", 2008, pp. 480-482, Elsevier, New York.
U.S. Appl. No. 12/379,239, filed Feb. 17, 2009, Taylor et al.
U.S. Appl. No. 11/075,690, filed Mar. 10, 2005, Taylor et al.
U.S. Appl. No. 12/654,147, filed Dec. 11, 2009, Taylor et al.
Jul. 14, 2014 Communication issued in European Application No. 11739229.0.
Mar. 11, 2014 Office Action issued in Chinese Application No. 201180044640.7 (with English Translation).
Jan. 28, 2015 Office Action issued in Chinese Application No. 201180044640.7.
May 21, 2015 Office Action issued in European Application No. 11739229.0.
Nov. 4, 2011 International Search Report issued in PCT/US2011/044210.
Nov. 4, 2011 Written Opinion issued in PCT/US2011/044210.
Taylor, Michael J. et al., "Viable Yield of Islets From Ischemic Porcine Pancreata is Improved Using Twenty-Four Hour Hypothermic Machine Perfusion Preservation," Jul. 27, 2008, p. 369, vol. 86, No. 2S.

(Continued)

*Primary Examiner* — Soren Harward
*Assistant Examiner* — Paul D. Pyla
(74) *Attorney, Agent, or Firm* — Oliff PLC

(57) ABSTRACT

Methods of isolating cellular products, such as pancreatic islets, may be used in diabetes research and therapeutic transplantation. The methods may involve providing a donor tissue having desired cells and undesired cells, perfusing the donor tissue with a perfusion solution, developing edema during perfusion of the donor tissue to form a swelled tissue, and separating the desired cells from undesired cellular material to obtain a cellular product. The methods may also include disrupting the tissue, and separating the desired cells from undesired cellular material to obtain the cellular product. The methods may result in an increased yield of cellular product that retains sufficient functional integrity to be useful as a transplantation resource.

27 Claims, 11 Drawing Sheets

(56) References Cited

OTHER PUBLICATIONS

Taylor, Michael J. et al., "Hypothermic Machine Perfusion Preservation of Porcine Pancreas Facilitates Islet Isolation," Nov. 22, 2007, p. 343, vol. 55, No. 3.
Baicu, Simona C. et al., "Modulating Biochemical Perturbations During 72-Hour Machine Perfusion of Kidneys: Role of Preservation Solution," Feb. 24, 2007, pp. 114-120, vol. 54, No. 1.

* cited by examiner

METHODS FOR INCREASING ISOLATION YIELDS OF CELLULAR PRODUCTS

CROSS-REFERENCE TO RELATED APPLICATION

This nonprovisional application claims the benefit of U.S. Provisional Application No. 61/365,103 filed Jul. 16, 2010. The disclosure of the prior application is hereby incorporated by reference in its entirety.

GOVERNMENT SUPPORT

The invention was supported, in whole or in part, by grants R44DK065508 and R44DK076326 from the National Institutes of Health. The Government has certain rights in the invention.

BACKGROUND

In modern medicine, cellular therapies, regenerative medicine and tissue engineering all involve technologies for harvesting, expanding, modifying and re-implanting live viable cells and tissues. A primary example is the transplantation of isolated pancreatic islets of Langerhans for the treatment of Type I (insulin dependent) diabetes. Ever since the first experimental attempts to ameliorate Type I diabetes by transplantation of allograft donor islets the field has been challenged by the need for improved methods of retrieving islets from donor pancreata. In fact, there is a considerable worldwide effort to further develop the concept for treating Type I diabetes by transplanting islets, but clinical application of the techniques developed in animal models is fraught with many challenges. The field of islet transplantation generally relies upon enzymatic digestion processes that destroys the extracellular matrix of the tissue, releasing the entrapped islets for further processing and purification. This widely practiced procedure has drawbacks due principally to the difficulty of controlling the digestive process to yield an optimum quantity of viable cells.

The source of the islets also remains a primary concern, and isolation from donor pancreases demands resolution of questions concerning the source, supply, and condition of the donor organs. Reliance upon an adequate supply of human organs for this purpose is considered futile, such that alternative sources are actively been sought (Bonner-Weir, S. et al., New sources of pancreatic beta-cells, Nat. Biotechnol. 23:857-861, 2005; Hering, B. J. et al., Prolonged diabetes reversal after intraportal xenotransplantation of wild-type porcine islets in immunosuppressed nonhuman primates, Nat. Med., 12:301-303, 2006; Inada, A.; Bonner-Weir, S. et al., How can we get more beta cells?, Curr. Diab. Rep., 6:96-101, 2006).

Various mammals are considered optimal candidates for xenogeneic islet transplantation. Of the potential mammals, pigs are considered the donor species of choice for xenogeneic islet transplantation for a number of compelling reasons. Pigs share many physiological similarities to humans and porcine insulin has demonstrated clinical efficacy for many years. Pigs are raised as a food source and provide an ethical source of donor islets by being housed in a controlled environment to ensure safety for porcine islet xenotransplantation. However, experiences in many laboratories over the past 10 years show that isolation of porcine islets appears to be more difficult (Finke, E., et al., Large scale isolation, function, and transplantation of islets of Langerhans from the adult pig pancreas. Transplant. Proc. 23:772-773, 1991; Giannarelli, R. et al., Preparation of pure, viable porcine and bovine islets by a simple method. Transplant. Proc., 26:630-631, 1994; Marchetti, P. et al., Automated largescale isolation, in vitro function and xenotransplantation of porcine islets of Langerhans, Transplantation 52:209-213, 1991; O'Neil, J. J. et al., The isolation and function of porcine islets from market weight pigs. Cell Transplant., 10:235-246, 2001; Toso, C. et al., Isolation of adult porcine islets of Langerhans. Cell Transplant., 9:297-305, 2000), compared with the isolation of human (Kenmochi, T. et al., Improved quality and yield of islets isolated from human pancreas using two-step digestion method, Pancreas 20:184-190, 2000), bovine (Figliuzzi, M. et al., Influence of donor age on bovine pancreatic islet isolation, Transplantation, 70:1032-1037, 2000), or rodent islets (Shapiro, A. M. et al., High yield of rodent islets with intraductal collagenase and stationary digestion—a comparison with standard technique, Cell Transplant., 5:631-638, 1996).

Porcine islets are less compact and tend to fragment during the isolation procedure and during prolonged periods of in vitro culture (Ricordi, C. et al., A method for the mass isolation of islets from the adult pig pancreas, Diabetes, 35:649-653, 1986). Moreover, the age, and even the strain, of the donor pig has been documented by several groups to markedly influence the islet isolation process, with young, so-called market size pigs (<6 months old) proving to be particularly difficult as a source of transplantable islets (Bottino, R. et al., Isolation outcome and functional characteristics of young and adult pig pancreatic islets for transplantation studies, Xenotransplantation, 14:74-82, 2007; Dufrane, D. et al., Impact of porcine islet size on cellular structure and engraftment after transplantation: Adult versus young pigs, Pancreas 30:138-147, 2005; Toso, C. et al., Isolation of adult porcine islets of Langerhans. Cell Transplant., 9:297-305, 2000). Islets from adult pigs (>2 years old) offered not only higher yields, but retained the ability to preserve intact morphology during the isolation process and culture, in association with higher functional properties after transplantation. Despite the challenge encountered by many groups attempting to isolate islets from young pigs, donor pigs of market weight (<80 kg=<12 months old) are preferred to retired breeders (>200 kg=>2 years old) due to their abundance, lower animal and husbandry costs, and they are more suitable to meet regulatory guidelines for donor tissue for xenotransplantation. The methods of this disclosure may improve the cellular product yield from donor tissues and improve the efficacy of hypothermic machine perfusion (HMP) of donor tissues, such as pancreata, prior to use, such as during islet isolation.

The scientific basis for hypothermic perfusion preservation of organs is founded upon the effect of temperature on all biologic and chemical processes, which are fundamentally slowed by a reduction of temperature. Hence the deleterious consequences of ischemia and anoxia can be attenuated by the application of hypothermia, which has provided the cornerstone of most of the effective methods of organ preservation in common use today. Hypothermic perfusion preservation is based upon the fundamental premise that devices can be designed to facilitate the replacement of blood in the circulation of an ex vivo organ with specially designed fluids to maximize the protective effects of hypothermia on the ischemic tissue.

Since the advent of clinical organ transplantation in the 1960's, a variety of perfusion machines have been developed principally for kidney preservation, but until recently these were not employed clinically due to the relatively high cost and complexity compared with simple cold storage techniques. Today, there is a growing use of machine perfusion for donor kidney preservation due to the reported effect of improved outcome using so-called "marginal" or "expanded criteria" donor organs. This technique therefore has a major potential impact upon increasing the numbers of organs available for transplantation. One of the commercially available machines (LifePort®; LifeLine Scientific) approved for clinical use for kidneys may be utilized in the methods associated with the present application improving the cellular product yield from donor tissues either with or without hypothermic preservation.

Earlier studies have demonstrated that hypothermic preservation of organs, such as the pancreas, by machine perfusion is feasible and may be safely extended to 24 and 48 h (Alteveer, R. J. et al., Hemodynamics and metabolism of the in vivo vascularly isolated canine Pancreas, Am. J. Physiol., 236:E626-E632, 1979; Florack, G. et al., Preservation of canine segmental pancreatic autografts: Cold storage versus pulsatile machine perfusion, J. Surg. Res., 34:493-504, 1983; Leeser, D. B. et al., Pulsatile pump perfusion of pancreata before human islet cell isolation, Transplant, Proc. 36:1050-1051, 2004; Tersigni, R. et al., Pancreaticoduodenal preservation by hypothermic pulsatile perfusion for twenty-four hours, Ann. Surg., 182: 743-748, 1975; Toledo-Pereyra, L. H., Hypothermic pulsatile perfusion: Its use in the preservation of pancreases for 24 to 48 hours before islet cell transplantation, Arch. Surg., 115:95-98, 1980; Moers, C. et al., Machine perfusion or cold storage in deceased-donor kidney transplantation, N. Engl. J. Med., 360:7-19, 2009; Rakhorst, G. et al., Revival of machine perfusion: New chances to increase the donor pool? Expert Rev. Med. Devices 2:7-8, 2005; Reznik, O. N. et al., Increasing kidneys donor's pool by machine perfusion with the LifePort-pilot Russian study, Ann. Transplant, 11:46-48, 2006; Taylor, M. J. et al., Current state of hypothermic machine perfusion preservation of organs: The clinical perspective, Cryobiology, in press).

Dedicated renal perfusion systems may be employed by the methods of the present disclosure after appropriate modifications are made to accommodate the characteristics of the respective organ, such as, for example, the physiologic low flow and pressure needs of the pancreas. The latter helps avoid excessive organ edema that postsegmental transplantation and reperfusion has been documented to result in subcapsular bleeding, hemorrhagic necrosis, venous congestion, and hemorrhagic pancreaticoduodenal secretions.

Transplantation of cellular products has been previously reported. For example, transplanted islets isolated from 24-h perfused dog pancreata have been reported to result in 60% recipient survival post transplantation, providing similar outcome to fresh islets implantation. Islets isolated from human pancreas after 13 h of cold static storage and 4 h of hypothermic pulsatile perfusion on a Waters RM3 system were characterized by higher viable yield and stimulation index relative to cells isolated from organs that sustained more than 8 h of static storage alone (Gondolesi, G. E. et al., Reduction of ischemia-reperfusion injury in parenchymal and nonparenchymal liver cells by donor treatment with DL-alpha-tocopherol prior to organ harvest, Transplant. Proc., 34:1086-1091, 2002).

These studies clearly provide the basis for a major clinical/commercial impact for new technologies that provide desperately needed improved methods of pancreas preservation to produce better yields of high quality islets. Clearly, islet transplantation is emerging as a viable option for the treatment of insulin-dependent diabetes mellitus, and clinical trials are under way at many centers around the world (Alejandro, R. et al., 2008 update from the Collaborative Islet Transplant Registry, Transplantation 86:1783-1788, 2008; and Shapiro, A. M. et al., International trial of the Edmonton protocol for islet transplantation. N. Engl. J. Med. 355:1318-1330, 2006). Accordingly, the demand for donor islets is escalating and will continue to grow. Thus, there is a need for higher quality and quantities of islets.

Despite many efforts to improve the technique of islet isolation, the field remains constrained by the limitations and vagaries of enzymatic digestion of a gland that comprises less than 5% endocrine tissue. Consequently, harvesting islets from a single donor pancreas often yields insufficient islet mass to reverse diabetes in a recipient, such that multiple donors often have to be considered for treating a single recipient.

The potential for xenotransplantation to relieve the demand on an inadequate supply of human pancreases depends upon the efficiency of techniques for isolating islets from the source pancreases (Hering, B. J. et al., The International Xenotransplantation Association consensus statement on conditions for undertaking clinical trials of porcine islet products in type 1 diabetes—executive summary, Xenotransplantation 16:196-202, 2009). However, at this time, procurement of donor pancreases for islet isolation and transplantation is not yet widely practiced due in part to concerns about postmortem ischemia upon functional islet yields.

SUMMARY

Methods are disclosed for isolating cellular products by application of hypothermic machine perfusion (HMP) and the development of interstitial edema while preserving the integrity of the cellular products, such as islets, which greatly increases the amount and quality of cellular products that may be retrieved compared with conventional methods applied to nonperfused donor tissues (i.e., fresh or static cold stored donor tissues).

In embodiments, a cellular product may be isolated by methods comprising developing edema during perfusion of the donor tissue. In such embodiments, developing edema during perfusion of the donor tissue may occur by increasing a first flow rate of the perfusion solution through the tissue to achieve a second flow rate, increasing a first perfusion pressure applied by the perfusion apparatus to the tissue to achieve a second perfusion pressure, and/or selecting a composition of the perfusion solution that causes edema of the tissue.

In embodiments, a cellular product, such as islets, hepatocytes, or cardiomyocytes, may be isolated by methods comprising: providing a donor tissue, developing edema during perfusion of the donor tissue to form a swelled tissue, and separating the desired cells from undesired cellular material to obtain a cellular product.

In embodiments, development of edema may occur by increasing a first flow rate of the perfusion solution through the tissue to achieve a second flow rate, increasing a first perfusion pressure applied by the perfusion apparatus to the tissue to achieve a second perfusion pressure, and/or selecting a composition of the perfusion solution that causes edema of the donor tissue, where the extent of edema may be assessed by monitoring buoyancy of the donor tissue, monitoring surface area of the donor tissue, monitoring a circumference of the donor tissue, monitoring weight and/or mass of the donor tissue, and or monitoring volume of the donor tissue.

In embodiments, a cellular product may be isolated by methods comprising providing a tissue having desired cells that are less prone to destructive freezing and undesired cells that are more prone to destructive freezing, freezing the tissue, disrupting the tissue, warming the tissue, and separating the desired cells from undesired cellular material to obtain the cellular product.

In embodiments, the cellular product may be isolated by methods comprising pre-treating a tissue such that desired cells are less prone to destructive freezing and undesired cells are more prone to destructive freezing, freezing the tissue, disrupting the tissue, warming the tissue, and separating the desired cells from undesired cellular material to obtain the cellular product.

In embodiments, the cellular product that retains sufficient functional integrity to be useful as a transplantation resource may be isolated by methods comprising surgically preparing an ex vivo tissue for vascular and ductal cannulation, cooling the tissue, equilibrating tissue with a cryoprotective agent, optionally freezing the tissue to a temperature from about −10° C. to about −200° C., optionally mechanically disrupting the tissue while keeping the tissue frozen, optionally thawing the tissue, filtering the tissue, washing the tissue, purifying the cellular product, such as by gradient purifying, and/or optionally culturing the cellular product.

In embodiments, the tissue may be pancreatic tissue and the cellular product comprises pancreatic islets. In embodiments, islets of a pancreas may be isolated by methods comprising infusing islet tissue with a cryoprotectant solution comprising a cryoprotective agent (CPA) via a vascular system, infusing the acinar tissue with an aqueous solution via a ductal system, freezing the pancreas, disrupting the pancreas, warming the pancreas, and separating the islets. In embodiments, pancreatic islet tissue retains sufficient functional integrity to be useful as a transplantation resource.

In embodiments, the donor tissue may be from the liver and the cellular product comprises hepatocytes. In embodiments, the donor tissue may be from the heart and the cellular product comprises cardiomyocytes.

In embodiments, developing edema during perfusion of the donor tissue comprises: increasing a first flow rate of the perfusion solution through the tissue to achieve a second flow rate, increasing a first perfusion pressure applied by the perfusion apparatus to the tissue to achieve a second perfusion pressure, and or selecting a composition of the perfusion solution that causes edema of the tissue. In embodiments, the methods of the present disclosure comprise: monitoring buoyancy of the donor tissue to assess the extent of edema, monitoring surface area of the donor tissue to assess the extent of edema, monitoring a circumference of the donor tissue to assess the extent of edema, monitoring mass of the donor tissue to assess the extent of edema, and/or monitoring volume of the donor tissue to assess the extent of edema.

Additional features and advantages of the present invention are described in, and will be apparent from, the following detailed description of embodiments.

DETAILED DESCRIPTION OF EMBODIMENTS

Figure 1:
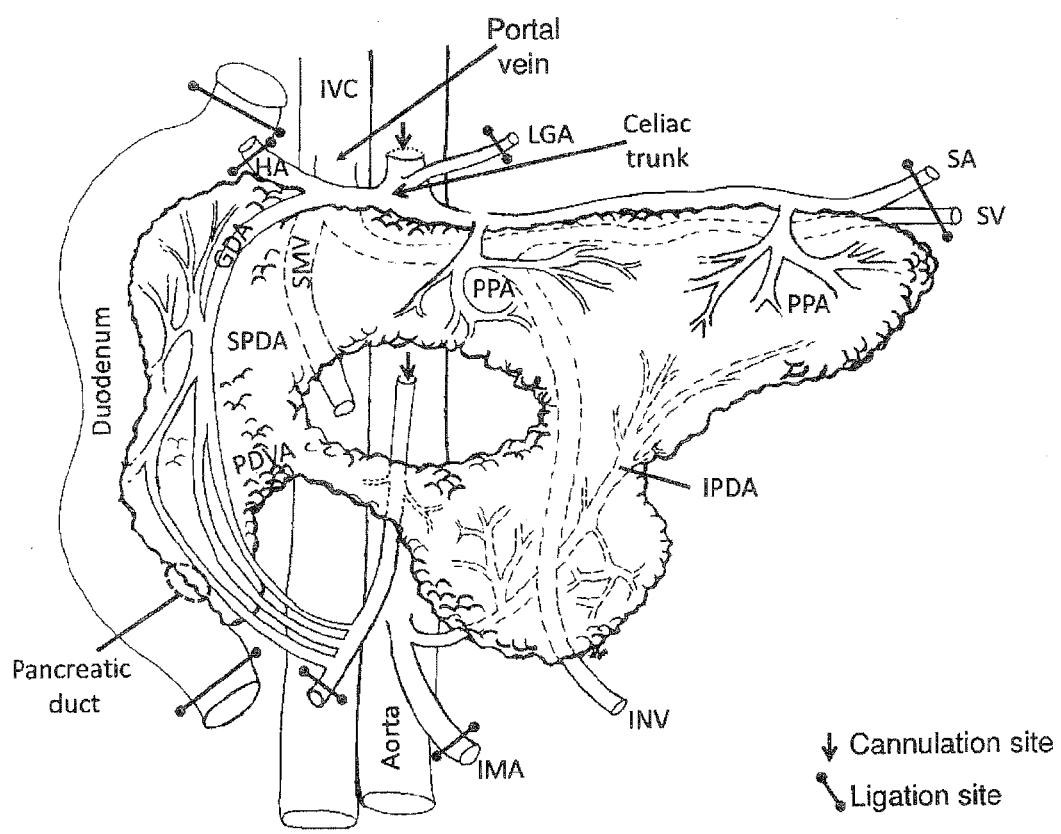
FIG. 1 is an illustration of a diagram showing the pancreas excised with a segment of the descending aorta for cannulation of the celiac trunk (CT) and superior mesenteric artery (SMA)

In embodiments, methods are disclosed for isolating cellular products by application of hypothermic machine perfusion (HMP) and the development of interstitial edema while preserving the integrity of the cellular products, such as islets, which greatly increases the amount and quality of cellular products that may be retrieved compared with conventional methods applied to nonperfused donor tissues (i.e., fresh or static cold stored donor tissues).

"Edema" is used herein to refer to an accumulation of an excessive amount of watery fluid in cells, tissues, or serous cavities.

"Tissue or organ" is used herein to refer to any natural or engineered biological tissue or organ, including, but not limited to, cardiovascular tissue, neuronal tissue, periodontal tissue, glandular tissue, islets of Langerhans, hepatocytes, cardiomyocytes, organ tissue, and organs, such as pancreas, bladder, kidney, breast, liver, intestine, heart and sections or pieces thereof. Such tissue may be obtained from any organism, such as a mammal, for example, humans or otherwise, including heart-beating donors, or non-heart-beating donors. Tissues may be used in whole or in-part, such as tissues that have been cut or sliced.

As used herein, the term "perfusion" means the flowing of a fluid through the tissue. Techniques for perfusing organs and tissues are discussed in, for example, U.S. Pat. No. 5,723,282 to Fahy et al., which is incorporated herein in its entirety.

The excision of a tissue for transplantation means that ischemia is total and inevitable even though the period may be brief. An immediate consequence of cessation of blood supply to an organ is deprivation of the supply of oxygen to the tissues, but anoxia (total) or hypoxia (partial) is only one of the many consequences of a lack of blood supply. A multifactorial cascade of events ensues following the initiation of ischemia. The pivotal event is ATP depletion, which occurs within the first few minutes of oxygen deprivation. This early event leads immediately to a shift from aerobic to anaerobic metabolism, which very quickly becomes self-limiting with the production of lactate and protons. Cell depolarization also occurs very early in the cascade leading to a breakdown of ion homeostasis, and a concatenation of other intracellular and membrane-associated events that eventually culminate in cell death by either apoptosis or necrosis.

The basic principle of cellular preservation for clinical application is to minimize the deleterious effects of ischemia and anoxia during the preservation interval. This can either be achieved pharmacologically by using a wide variety of cytoprotective drugs, and/or by reducing temperature. Interestingly, conventional wisdom teaches us that there is no single drug, or cocktail of drugs, that can so safely and effectively suppress metabolism and provide ischemic protection for multiple tissues and organs as the application of hypothermia can. Accordingly, the focus changes to control the environment of cells to optimize hypothermic preservation.

In embodiments, the methods disclosed herein implement a new approach that utilizes advances in perfusion technology and optionally combines those advances with hypothermic blood substitute solutions to improve $O_2$-delivery by means of PFC-augmentation. This approach circumvents several recognized shortcomings in the present modes of clinical organ storage, the most notable of which is the demonstrated low penetration of PFC and oxygen using the conventional two layer method (TLM).

In the specific case of pancreas preservation prior to islet isolation, a salutary effect of HMP on islet yield in a juvenile porcine model has emerged. However, given the vulnerability of islets to even short periods (<10 h) of cold ischemia, the new approaches described herein extend tolerance to ischemia by circumventing the constraints recognized in conventional techniques of pancreas preservation. The innovation revolves around the application of one or more of three individually important components of organ preservation, namely machine perfusion for inducing development of edema; hypothermic blood substitution, and improved oxygen delivery by PFC augmentation.

Hypothermic Machine Perfusion (HMP): Conventional methods of organ preservation for transplantation rely principally upon static cold storage on ice, a relatively simple and economic technique that has been used for several decades. However, modern day demands for increasing the numbers of organs available for transplant has led to a resurgence of interest in hypothermic perfusion preservation (HPP) of organs because perfusion techniques provide significant advantages over static cold storage. In this context HPP is based upon the fundamental premise that devices can be designed to facilitate the replacement of blood in the circulation of an ex vivo organ with specially designed fluids to maximize the protective effects of hypothermia on the ischemic tissue. This approach has the potential, and has already been shown in many applications, to circumvent some of the recognized shortcomings of conventional cold storage. However, in the field of pancreas preservation, particularly as it applies to source organs for islet isolation, static cold storage imposes severe restrictions upon the yield and quality of islets obtained from a single donor pancreas. For example, introducing a perfluorochemical layer to purportedly increase the supply of oxygen to the ischemic organ has failed in static cold storage methods to provide the added protection.

In embodiments, the methods disclosed herein utilize a combination of technologies in HMP and HBS along with the merits of PFC oxygenation to generate a new hybrid technique that solves the problems of static cold storage methods having a perfluorochemical layer. Selection of the baseline medium or perfusate in which to deliver the PFC as an emulsion also demands consideration of what will be optimal for the respective cell (e.g., pancreatic cells, cardiac cells, etc.,) preservation under hypothermic conditions. To this end, this disclosure includes the preparation of preservation solutions designed as hypothermic blood substitutes.

Hypothermic blood substitutes as preservation media: Traditionally, a variety of organ preservation solutions have been developed.

U.S. Pat. Nos. 5,643,712, 5,699,793, 5,843,024 to Brasile and Nos. 5,599,659, 5,702,881 to Brasile et al., the disclosures of each of which are incorporated herein by reference in their entireties, describe separate resuscitation and preservation solutions for tissues and organs. The Brasile patents disclose compositions that may be used in methods of this disclosure.

Taylor et al. have formulated and evaluated two solutions designated Hypothermosol™-purge (HTS-P) and Hypothermosol™-maintenance (HTS-M). Some aspects of these solutions are described in U.S. Pat. Nos. 5,405,742 and 5,514,536 to Taylor, the disclosures of both of which are incorporated herein by reference in their entireties. The Taylor patents disclose compositions that may be used in methods of this disclosure.

The protective properties of solutions such as the Unisol® family of solutions (as described in U.S. Pat. Nos. 6,492,103 and 6,994,954, entitled "System for organ and tissue preservation and hypothermic blood substitution" to Taylor, the disclosures of which are hereby incorporated by reference in their entireties) may be used in methods of this disclosure. In embodiments, Unisol may be utilized as the vehicle solution for emulsifying PFCs to significantly increase its oxygen delivery capacity, in addition to cytoprotective additives.

In embodiments, the principal solution may be a hyperkalemic, "intracellular-type" solution designed to "maintain" cellular integrity during hypothermic exposure at the nadir temperature (<10° C.).

Increasing oxygen delivery to tissues during hypothermic storage and the role of PFCs: The Unisol® "maintenance" solution was developed and tested at temperatures in the range of 7-10° C., which conforms with the temperature range in which ATP reserves can be re-established if an adequate supply of $O_2$ is maintained by continuous perfusion. For example, numerous investigations have suggested that oxygen supply is essential during hypothermic preservation of livers.

The rapid depletion of adenine nucleotides during cold storage of organs at 0-2° C. (e.g. conventional static cold ice-storage) may be suggestive that mitochondrial function is severely impaired by hypothermia. These levels of $O_2$ may need to be sustained during perfusion to ensure the highest quantify and quality cellular products, such as islets, and the use of PFCs allows for this to be accomplished.

PFCs are hydrocarbons in which all or most of the hydrogen atoms are replaced with fluorine (e.g., perfluorocarbons). They have twice the density of water and a high capacity for dissolving respiratory gases. The solubility of dissolved oxygen in PFC is approximately 25 times greater than in blood or water. The ability of PFCs to release oxygen in accordance with Henry's Law is not significantly influenced by temperature, making them ideal for delivering oxygen during hypothermic organ preservation. This is also supported by recent demonstrations that the gas-dissolving and gas-unloading properties of perfluorocarbon were necessary in a peritoneal perfusion application for systemic oxygenation since the same effect was not obtained when saline solution alone was employed as the perfusate. However, the use of perfluorocarbon under hypothermic conditions has been limited.

In embodiments, the methods of the present disclosure comprise preventing anaerobic glycolysis in the donor tissue. In embodiments, preventing anaerobic glycolysis in the donor tissue may comprise introducing perfluorochemicals into the perfusion solution and/or preventing oxygen deprivation/depletion in the donor tissue. For example, preventing oxygen deprivation/depletion in the donor tissue may comprise introducing perfluorochemicals into the perfusion solution and oxygenating the perfusion solution.

In embodiments, the methods of the present disclosure comprise perfusion with a perfusion solution, where the perfluorochemicals represent from about 10% to about 90% of the total weight of the perfusion solution, the perfluorochemicals represent from about 10% to about 80% of the total weight of the perfusion solution, the perfluorochemicals represent from about 20% to about 70% of the total weight of the perfusion solution, or the perfluorochemicals represent from about 30% to about 60% of the total weight of the perfusion solution.

In embodiments, the methods of the present disclosure may comprise satisfying the $O_2$ demand of a donor tissue throughout a preservation interval/process occurring from the time the perfusion apparatus is connected to the donor tissue to the time perfusion apparatus is disconnected from the donor tissue. Such methods may comprise replenishing $O_2$ content in the perfusion solution during perfusion, increasing $O_2$ content in the perfusion solution during perfusion, and/or decreasing $CO_2$ content in the perfusion solution during perfusion. The levels of $O_2$ and $CO_2$ in the tissue and/or perfusion solution may be monitored by any known method.

In embodiments, the methods of the present disclosure comprising monitoring the extracellular space in the donor tissue by microdialysis. For example, monitoring the extracellular space in the donor tissue by microdialysis may comprise implanting a dialysis probe into the donor tissue and assessing the concentration of interstitial fluid components. Such a dialysis probe may comprise a semi-permeable bio-compatible membrane as the active part. In embodiments, in the methods of the present disclosure, the concentration of interstitial fluid components is assessed periodically. Exemplary interstitial fluid components include any analyte contained in the perfusion solution or tissue, including one or more selected from the group consisting of glucose, lactate, pyruvate, glycerol, ATP, $O_2$ and $CO_2$. In embodiments, the methods of the present disclosure include assessing the oxygen consumption rate of the donor tissue before the perfusion apparatus is connected to the donor tissue, assessing the oxygen consumption rate of the donor tissue after the perfusion apparatus is connected to the donor tissue, and/or monitoring the oxygen consumption rate of the donor tissue after the perfusion apparatus is connected to the donor tissue.

As discussed below, the application of one or more of these three organ preservation strategies outlined above minimizes damage and cell death in the donor tissue or organ, such as the pancreas, which may promote an increase the overall islet yield. This strategy has the potential of significant benefits for other transplantable organs all of which suffer ischemic injury during cold storage.

As discussed above, procurement and preservation of pancreata is important for islet isolation as a prelude to islet transplantation as an option for the treatment of Type I diabetes mellitus. Pancreas perfusion can further be applied for the preservation of organs exposed to warm ischemia prior to islet isolation and to optimize pancreas preservation solution for a better islet yield and quality. The above-mentioned organ preservation prior to islets isolation may allow for more time for proper donor-recipient matching and quality control of isolated cells, and offers the possibility of banking cells for increased availability to clinicians. Hypothermic machine perfusion provides an answer to the pancreas shortage for transplantation by improving flow and reducing vascular resistance and allowing for pancreas quality evaluation prior to transplantation.

Physiologically, the pancreas is a low flow organ. In embodiments, the methods of this disclosure may comprise pancreas perfusion, which may be based on a low constant pressure (about 10 mmHg or less, such as from about 1 mmHg to about 10 mmHg) driven flow. The present design of the LifePort® may not accommodate infusion pressures of less than 10 mmHg. Thus, lower pressure values may be installed in order to reach the desired infusion pressures of less than 10 mmHg for the methods disclosed herein for preserving pancreata for transplantation without inducing irreversibly high levels of edema that may be detrimental to the organ and/or recipient. Controlled development of edema and better perfusion outcome for both islets isolation and whole pancreas transplantation may be better attained by employing a constant flow regime as opposed to constant pressure. In embodiments, the driven flow rate values may be selected in accordance with organ characteristics and quality (such as warm ischemic exposure, size, species, etc.).

In alternative embodiments, the methods of perfusion may be based on a high (about 10 mmHg or more, such as from about 10 mmHg to about 60 mmHg) constant pressure driven flow.

In embodiments, the methods described herein employ an apparatus for perfusing one or more organs or tissue (hereinafter generally referred to as donor tissues). An exemplary apparatus is described in U.S. patent application Ser. No. 12/379,239, which is a division of U.S. patent application Ser. No. 11/075,690, filed Mar. 10, 2005 (issued as U.S. Pat. No. 7,504,201 on Mar. 17, 2009) the entire disclosures of which are hereby incorporated by reference in their entireties. In embodiments, the methods described herein employ the LifePort® platform transporter or a modified LifePort® platform transporter in order to accomplish hypothermic machine perfusion (HMP) of a donor tissue (such as the pancreas).

In embodiments, HMP may result in uniform fluid accumulation within the donor tissue that in turn may provide a disrupted extracellular space with beneficial effects for islet isolation without compromising islet viability and function. The methods of this disclosure, described herein with respect to juvenile porcine pancreata, may be easily applied to human and adult porcine donor pancreases, the latter being regarded as the source of choice for xenogeneic islet transplantation, and/or other various donor tissues of interest, such as the heart and/or liver. The successful methods described herein rely strongly upon the details of pancreas surgical procurement, cannulation and perfusion on the LifePort®. Based on these methods, pancreas hypothermic perfusion optimization may be achieved for development of methods of organ evaluation and quality control during perfusion in order to reliably select high quality pancreases for clinical transplantation.

A major technological issue to be addressed in applying the established "LifePort" kidney perfusion technique to the pancreas is the different perfusion parameters required by the pancreas since this is a low flow, low pressure organ compared with the kidney. Typically, the optimum perfusion parameters for a kidney on a LifePort® machine, which by design is a pressure-controlled device, are a set perfusion pressure of 25-40 mmHg (typically produces a flow rate of 100-150 ml/min). These perfusion parameters may impact the fluid exchange between the vascular and interstitial compartments of the organ and hence the degree of edema sustained during the perfusion interval. The method described here demonstrates the adaptation of the LifePort® machine for pancreas perfusion with an emphasis on developing a specific amount of Edema. In embodiments, the LifePort® machine for pancreas perfusion may be adapted to operate at a low pressure setting (about 10 mmHg or less, such as in the range from about 10 mmHg to about 2 mmHg, or in the range from about 8 mmHg to about 4 mmHg)-controlled perfusion of porcine pancreas as a prelude to pancreas processing for islet isolation.

In embodiments, the LifePort® machine for pancreas perfusion may be adapted to operate a flow rate of less that 150 ml/min, such as less than 100 ml/min, or from about 10 ml/min to about 100 ml/min, such as from about 15 ml/min to about 50 ml/min, or from about 20 ml/min to about 30 ml/min.

In embodiments, the LifePort® machine for pancreas perfusion may be adapted to operate at a high pressure setting (about 10 mmHg or more, such as in the range from about 10 mmHg to about 60 mmHg, or in the range from about 20 mmHg to about 50 mmHg)-controlled perfusion of porcine pancreas as a prelude to pancreas processing for islet isolation. In embodiments, the LifePort® machine for pancreas perfusion may be adapted to operate a flow rate of less that 200 ml/min, such as less than 150 ml/min, or from about 10 ml/min to about 150 ml/min, such as from about 50 ml/min to about 120 ml/min, or from about 60 ml/min to about 110 ml/min.

In embodiments, the LifePort® machine may ensure proper cold static storage of the donor tissue or organ if the pump fails and the fluid transport through the organ stops. For example, inside the closed transporter, a properly filled ice container may be maintained at a temperature below about 6° C. for more than 24 h, without ice replenishment. The LifePort® transporter may be programmed to allow for re-circulation of a desired perfusate for under predetermined conditions, for example, the transporter may be programmed to allow one liter of perfusate re-circulation at 5-7° C. by a pulsatile (30 pulses/min) constant low pressure (about 10 mmHg) flow.

The LifePort® pulsatile perfusion system has been successfully employed for small pig pancreas hypothermic ex-vivo perfusion. The system is designed and FDA cleared for kidney hypothermic perfusion/preservation for clinical transplantation. Using the kidney system the whole pancreas of young porcine donors (25-32 kg, 2 months old) may be continuously perfused in a closed loop while being completely immersed in the perfusion solution inside the organ bath. The latter also serves as a solution reservoir, the perfusate being drawn out by the pump, forced to go through the filter, bubble trap and the infusion port before returning to the pancreas and organ cassette. Pancreas submersion in the temperature-controlled perfusate helps eliminate temperature gradients across the organ surface and ensure high quality hypothermic preservation.

Embodiments of the invention may provide an improved method of isolating cellular products, which may be more consistent and reliable than conventional methods that rely on enzyme digestion. Embodiments may also provide methods that yield an optimum quantity of desired cells that retain sufficient functional integrity to be useful as a transplantation resource.

In embodiments, methods disclosed herein may be used to isolate any cellular product for therapeutic use and research, as long as the desirable and undesirable cells have, or can be treated to promote, development of edema. Such methods may allow the preservation of the integrity of the islets in addition to greatly facilitating islet isolation to the extent that the yield of cellular product may significantly increase (in some situations at least about double the yield or even triple the yield) compared with the yield of cellular product obtained from nonperfused tissues and even fresh tissues.

In embodiments, a cellular product may be isolated by methods comprising developing edema during perfusion of the donor tissue by increasing a first flow rate of the perfusion solution through the tissue to achieve a second flow rate, increasing a first perfusion pressure applied by the perfusion apparatus to the tissue to achieve a second perfusion pressure and/or selecting a composition of the perfusion solution that causes edema of the tissue.

In embodiments, development of edema in donor tissues to form a swelled tissue may occur by application of hypothermic machine perfusion (HMP). The application of donor tissue HMP, such as the pancreas HMP, as a prelude to islet isolation also capitalizes upon the some of benefits of HMP demonstrated for other various organs (principally the kidney) as a means of better preservation during extended periods of storage, especially for suboptimum organs. In addition, an unexpected salutary effect of machine perfusion applied to the application of cellular product harvesting, such as islets, has emerged.

The progressive development of edema during extended machine perfusion of organs is a phenomenon that is generally regarded as undesirable. In fact, steps are usually taken to minimize the problem by adjusting the mechanical perfusion parameters such as flow and pressure, as well as the composition of the perfusate, to minimize the development of interstitial edema. In resolving a technical problem with respect to cannulation of the donor tissues (in this case the pancreas) that affects the efficiency of perfusion, it was determined that 24 h of HMP resulted in moderate edema in the gland compared to the controls that were simply flushed with and immersed in cold UV-Viaspan solution. However, contrary to expectations, development of edema, such as up about 280% (i.e., a 180% gain in the particular parameter that is monitored to assess the extent of edema, such as, for example, weight, mass, circumference, buoyancy, and/or volume), or up to about 250%, or up to 150% to did not prove deleterious to cellular product harvesting, but was observed to be of considerable benefit by correlating with a more efficient disruption of the pancreas during enzymatic digestion to yield a significantly greater number of islets.

In embodiments, developing edema during perfusion of the donor tissue to form a swelled tissue may result in a swelled tissue exhibiting a weight, mass, circumference, surface area, buoyancy, and/or volume about 110% (i.e., gain in weight, mass, circumference, surface area, buoyancy, and/or volume of about 10%) of that of the initial or original non-perfused donor tissue, such as from about 120% to about 280% (i.e., gain in weight, mass, circumference, surface area, buoyancy, and/or volume of from about 20% to about 180%), or from about 130% to about 250% (i.e., gain in weight, mass, circumference, surface area, buoyancy, and/or volume of from about 30% to about 150%). In further embodiments, the swelled tissue has a mass that is less than 300% of an initial non-perfused mass of the donor tissue, the swelled tissue has a volume that is at least 110% of an initial non-perfused volume of the donor tissue, the volume of the swelled tissue is from about 150% to about 250% of the volume of the donor tissue, the volume of the swelled tissue is from about 120% to about 280% of the volume of the donor tissue, wherein the volume of the swelled tissue is from about 130% to about 250% of the volume of the donor tissue, or the swelled tissue has a volume that is less than 300% of an initial non-perfused volume of the donor tissue.

It is believed the presence of a predetermined amount of edema causes sufficient disruption to the extracellular matrix and architecture of the pancreatic gland that the subsequent distension and digestion of the gland proceeds more effectively. This is evidenced by significantly shorter digestion times (Table 3; below), a more homogeneous digestion product (FIG. 4), and better gradient purification resulting in higher yields and purity of the final islet preparation. The structure and function of the islets per se did not appear to be compromised by the level of tissue edema encountered in these studies. Concerns that a change in the hydration of the isolated islets due to HMP might alter the buoyant density of the islets and thereby alter their ability to be separated from exocrine tissue on a density gradient did not appear to be a problem. This may presumably be due to the fact that any inherent edema in the islets is counteracted by the pregradient incubation in UW solution, which is a hypertonic medium that would dehydrate the islets during the 30-min cold incubation prior to loading on the density gradient for purification, which is generally used in islet isolation protocols (Lakey, J. R. T., Technical aspects of islet preparation and transplantation, Transpl. Int., 16:613-632, 2003; Lakey, J. R. T.; Current human islet isolation protocol, Chuo-ku, Osaka: Medical Review Co. Ltd., 2004; the disclosures of which are hereby incorporated by reference in their entireties).

The morphological integrity of the islets in situ in the preserved pancreata may be evaluated by taking wedge biopsies at the end of a preservation interval. Changes associated with ischemia and the mode of preservation are illustrated and discussed with respect to FIG. 5. Dithizone staining of both the digest samples and purification fractions may be used to evaluate the gross structure, purity and numbers of islets in the respective samples. FIG. 4F shows the typical appearance of the highest purity preparations obtained from the HMP-treated pancreases. The islets have an irregular cluster shape that has been described as "grape-like" (Rijkelijkhuizen, J. K., et al., Pretransplant culture selects for high-quality porcine islets, Pancreas 32:403-407, 2006) and this appearance may be characteristic of islets isolated from young pigs, reflecting the irregular shape observed in the endogenous pancreas prior to isolation (Bottino, R. et al., Isolation outcome and functional characteristics of young and adult pig pancreatic islets for transplantation studies, Xenotransplantation 14:74-82, 2007). This characteristic irregular, fragmented appearance of islets from young pigs contrasts sharply with the more normal regular rounded shape of islets from adult pigs and may not a reflection of the method of preservation. FIG. 4B shows that islets from the fresh control pancreases have the same morphology.

The unanticipated mechanical benefit of HMP described above may be achieved without compromising the quality of the harvested islets. The data presented in the Examples section demonstrates that the functional ability, in terms of their insulin secretory index, of the islets isolated from the perfused pancreases in which a moderate amount of edema has been developed is equivalent to that of the controls including fresh pancreas. Moreover, the insulin content was significantly higher than the control group comprising pancreases stored statically in cold UW-Viaspan solution, which is currently the standard method employed clinically. These effects and standards of preservation may be achieved using either of two proprietary solutions, KPS1 and UNISOL-UHK.

Further improvements and benefits to this technique may occur by optimizing the composition of these baseline perfusates by adding cytoprotective agents design to minimize preservation and reperfusion injury, and/or PFCs. For example, cytoprotective additives may be additives displaying efficacy during low temperature preservation and therefore a high probability they will have a positive impact on the quality of pancreas preservation during hypothermic machine perfusion, such as antioxidants, anti-apoptotic agents and trophic factors.

In embodiments, the methods of the present disclosure comprise perfusing the organ and/or tissue with a perfusion solution comprises cytoprotective additives, such as one or more antioxidants, anti-apoptotic agents and trophic factors. Such a perfusion solution may be any perfusion solution, such as any perfusion solution described in the present disclosure, including hypothermic blood substitutes, including those comprising: one or more cytoprotective agents, and perfluorochemicals.

In embodiments, the methods of the present disclosure may comprise a step of increasing the ATP levels in the donor tissues during perfusion and/or a step of introducing cytoprotective agents during perfusion of the donor tissue for preventing cold-induced cell death of the donor tissue. In embodiments, the methods of the present disclosure may comprise a step of introducing cytoprotective agents during perfusion of the donor tissue for preventing cells of a donor tissue, such as a pancreas, from entering destructive pathways. For example, the methods may comprise introducing cytoprotective agents during perfusion of the donor tissue for inhibiting mitochondrial dysfunction in cells of a donor pancreas.

Antioxidants: Oxygen-derived free radicals (ODFR) have been the focus of attention as mediators of various tissue injuries and particularly microvascular injury. It is possible for the production of injurious free radicals to be enhanced during cold storage, it is important to appreciate that the resultant cell damage may not occur entirely at the low temperature. On the contrary there is a growing body of evidence that reintroduction of oxygenation via a regular blood supply upon rewarming and reperfusion provides a powerful impetus for further oxidative stress. A principal pathway is the stimulation of enzymically driven radical reactions such as the xanthine/xanthine oxidase system involving the interaction of ATP catabolic products with molecular oxygen. Vascular endothelial cells are thought to be particularly vulnerable to this type of injury mediated by free radical generation by this so-called "respiratory burst" mechanism. Nevertheless, low concentrations of molecular oxygen such as that dissolved in organ preservation solutions may be sufficient to support the generation of free radicals during prolonged storage. Therefore, without the proper balance of antioxidants, cold exposure may set the stage for a progressive development of tissue injury as a result of reactions and processes that occur during hypothermia.

In embodiments, the antioxidants may be present in a sufficient amount to substantially eliminate cellular damage and/or oxidative stress.

Whilst cells employ a number of repair mechanisms to recover from injuries occurring as a result of free radical activity, cell survival depends upon whether salvage pathways are overwhelmed or whether a point of irreversible damage is reached during the storage/reactivation process such that cell death becomes inevitable. Accordingly, in embodiments, the antioxidants, and amounts thereof, are selected to circumvent oxidative stress and reperfusion injury under both hypothermic and normothermic conditions. Exemplary antioxidants may include dibutyryl-cAMP (db-cAMP), α-tocopherol (Vitamin E), Trolox™, and HYPOTHERMOSOL plus both EDTA and Vitamin E.

Anti-Apoptotic Agents: While many of the diverse stresses known to cause necrotic cell death have also been reported to induce apoptosis in a variety of cells, the role of low temperatures as a possible stimulus of programmed cell death has only recently begun to emerge. It is now established that apoptosis plays an integral role in cell death induced by the rigors of both hypothermia and cryopreservation. More specifically, apoptosis has been identified to be directly associated with delayed-onset cell death (DOCD). This is defined as death associated with cold exposure that is not apparent immediately upon rewarming, but extending over the post-exposure recovery period. Recent research into the causative apoptotic and necrotic pathways responsible for low temperature induced DOCD has identified the contribution of multiple apoptotic pathways, including receptor- and mitochondrial-induced apoptosis. Investigations into these pathways, their progression, and their induction stressors has begun to facilitate new methods for improving preservation efficacy through the modulation of the cellular and molecular responses of a cell undergoing preservation (both hypothermic and cryopreservation).

Incorporation of specific apoptotic protease inhibitors in preservation media has now been reported to markedly improve the survival of a variety of cells and tissues. Furthermore, investigation into the modification of the carrier medium from that of standard extracellular-type culture media with, or without cryoprotectants, to that of specifically designed intracellular-type preservation solutions such as Unisol™, or its predecessor HYPOTHERMOSOL, have led to studies showing significant improvement in preservation efficacy.

Anti-apoptotic agents may be selected from those that possess recognized antioxidant activities and hence implied anti-apoptotic activity. For example, reduced glutathione is a component of both formulations as a multifaceted molecule that is also known to fulfill a natural role in the regulation of apoptosis, bongkrekic acid (BA) has been shown to be a potent inhibitor of mitochondrial permeability transition (PT) pores that form during apoptosis. In addition, BA can inhibit cytochrome c release that is influenced by Bax, a pro-apoptotic protein 85. BA, a stable inhibitor of PT, has been shown to increase cell viabilities and protein production levels following virus infection. With respect to the inhibition of caspases, a variety of compounds have been shown to be effective for mammalian cells in culture. Other exemplary compounds include, P35, which confers irreversible inhibition to a large number of caspases, and Z-VAD- .fmk (or its latest broad-spectrum counterpart, Q-VD-OPH), which has the ability to inhibit both the intrinsic and extrinsic pathways.

Trophic Factors: Many cell signaling pathways retain activity at very low temperatures and can be affected by trophic factor administration. Trophic factor deprivation disrupts many aspects of cell function and is well known to induce apoptosis and cell death in a wide variety of cultured cells. Trophic factor supplementation (TFS) leads to a markedly improved outcome in kidney storage an influence cold ischemic injury by interaction with the tissue during cold storage and not merely by being present during rewarming and reperfusion. Exemplary tropic factors, which may be employed include, for example, Insulin-like growth factor-1 (IGF-1) Epidermal growth factor (EGF), Bovine neutrophil peptide-1 (BNP-1), also referred to as bactenecin 98, Substance P (SP), which has mitogenic effects for a variety of cell types and stimulates DNA synthesis in ocular cell lines, EGF, a polypeptide growth factor (its effects may be additive or synergistic with other growth factors and cytokines), and insulin like polypeptide growth factors (IGFs), such as IGF-1.

In embodiments, the PFCs may possess one or more of the following qualities: (1) the ability to dissolve large quantities of many gases, (2) can transport these gases to diffuse across distances, (3) are non-toxic, (4) biologically inert, (5) biostatic liquids at room temperature. In embodiments, PFCs with densities of about 1.5-2.0 g/mL and high solubilities for oxygen and carbon dioxide may be selected.

In embodiments, the cellular product may be isolated by pre-treating a tissue such that desired cells are less prone to destructive freezing and undesired cells are more prone to destructive freezing as described in U.S. application Ser. No. 12/654,147, entitled "Method for Isolating Cellular Products by Cryopreservation," to Michael J. Taylor et al., which is hereby incorporated by reference in its entirety.

In embodiments, cryopreservation may be applied to selectively preserve the desired cells and/or destroy the undesired cells. Cryopreservation is a complex process of coupled heat and mass transfer, generally executed under non-equilibrium conditions. Simply freezing cells or tissues generally results in dead, nonfunctional materials.

In embodiments, the method comprises pre-treating donor tissues such that (1) the desired cellular product is less susceptible to events resulting in cell destruction, such as destructive freezing, and/or (2) the undesired tissue is made more susceptible to events resulting in cell destruction, such as destructive freezing. For example, when the donor tissue is a pancreas, the pre-treatment may occur by differential perfusion such that the destruction of acinar tissue is maximized while islet tissue is preserved. In such embodiments, islet tissue may be infused with a cryoprotectant solution comprising a cryoprotective agent (CPA) via a vascular system, such as through celiac trunk and superior mesenteric artery; after adequate equilibration of islet tissue, acinar tissue may be infused with an aqueous solution through pancreatic ducts.

In embodiments, the pretreatment the donor tissue may occur under controlled conditions to preferentially equilibrate the cellular product with in within the tissue. For example, pre-treating the pancreas may occur under controlled conditions to preferentially equilibrate the islet tissue within the pancreas gland at a temperature of from about 2° C. to about 35° C. Furthermore, perfusion may be maintained sufficiently long to allow equilibration of the islet tissue, but not the whole gland, with the permeating CPA. For example, perfusion may be maintained for a period of about 20 min. to about 70 min., such as about 25 to 35 min. or about 30 min. The rationale for this step is to deliver sufficient CPA to the islet tissue to protect it against freezing injury during subsequent cooling or freezing of the pancreas, which may occur during preservation and/or transport.

In embodiments, for a variety of reasons, such as preservation, transport, and/or disruption, the donor tissue may be cooled to a sufficient temperature to attenuate metabolism, such as a temperature of from about 15° C. to about −20° C., such as from about 10° C. to about −10° C., or from about 10° C. to about 0° C. In embodiments, for a variety of reasons, such as preservation, transport, and/or disruption, the donor tissue may be frozen to a temperature of from about −10° C. to about −200° C., such as from about −40° C. to about −170° C., or from about −80° C. to about −130° C. In embodiments, the cooling rate may be from about 0.5° C./min. to about 5° C./min. In embodiments, freezing and/or cooling the donor tissue may occur at a cooling rate of from about 1° C./min. to about 20° C./min., such as from about 6° C./min. to about 15° C./min.

In embodiments, the rate of cooling and/or freezing the donor tissue coupled with a rapid warming rate (such as the above rates for cooling and freezing multiplied by a factor of at least 1.5, such as a factor in the range from 1.5 to 10, such as a factor of 2, or 3, or 4, or 5) during warming of the donor tissue may provide optimum conditions for recovery of functional islet tissue. Warming of the donor tissue may be achieved by, in embodiments, direct immersion in a warm medium, such as an osmotically-buffered medium.

In embodiments, the extent of equilibration with CPA may or may not reach completeness, which may be beneficial because the conditions for full equilibration of islets in situ may not be easily determined in relation to the requirement for minimal permeation of the CPA into the exocrine cells.

In embodiments, the donor tissue may be divided into smaller pieces, fractured, and/or fragmented. In order to enhance fracturing of a donor tissue, such as the pancreas, volumetric warming may be combined with the addition of a compressed-air heat exchanger immersed in a hot water bath. In embodiments where the donor tissue is cooled or frozen on a preservation or transport platform, this may enable thawing of the donor tissue without the need to remove it from the platform. Donor tissue dividing or fracturing may occur at any time before exposure to the digestive enzyme, such as during warming of the donor tissue.

In embodiments, it may be advantageous to expose the donor tissue to various doses of a digestive enzyme to assist in connective tissue dispersion to allow release of the cellular product, such as islets (which optionally may be cryoprotected islets) from the disrupted tissue.

In embodiments, after the extent of edema has reached a predetermined level, such as a level of edema where the there is gain in weight, mass, circumference, surface area, buoyancy, and/or volume of up to about 200% (i.e., if the initial or original weight, mass, circumference, surface area, buoyancy, and/or volume of the tissue is X (such as 100 grams), a gain of about 200% would result in a final weight of 3× (300 grams), such as a gain of up to about 150%, or a gain of up to about 100%, the donor tissue may be disrupted to release cellular product from the disintegrated donor tissue. In embodiments, disrupting the donor tissue may occur while the donor tissue is frozen, while the donor tissue is warming, and/or after the tissue reaches room temperature. In embodiments, the disruption may be achieved by mechanical stress, thermo-mechanical stress induced by differential expansion, thermo-mechanical stress induced by steep temperature gradients, and thermo-mechanical stress induced by volume change upon freezing, via a digestive enzyme, or a combination thereof.

Thermo-mechanical stress may be the outcome of the tendency of material to contract upon freezing, which may be driven by three different effects: volume change upon freezing as described above, steep temperature gradients, and differential expansion in composite materials. In practice, two or more of the above effects may be acting in concert.

In other embodiments, disrupting the donor tissue may be achieved by mechanically fracturing a frozen donor tissue. For example, this may be accomplished in two stages. The first stage may be to physically split the frozen donor tissue into pieces, for example, with a hammer and chisel. The second stage may be to grind the frozen tissue pieces while immersed in warm water or isotonic medium, for example, by using an electric ice crusher or blender. This may also serve to effect rapid warming and dilution of a cryoprotectant, if included, at the same time as mechanically grinding the tissue.

In embodiments, the method further comprises separating the cellular product from the undesired donor tissue material. Separation of the cellular product may be achieved, for example, by filtration, density gradient separation, tissue culture, or a combination thereof. Filtration may be performed using a filtration apparatus, such as a stainless steel mesh (tea strainer). Separation may include washing the filtered donor tissue with a medium containing a protease inhibitor, such as PEFABLOC®, and a deoxyribonuclease, such as PULMOZYME®, such that harmful endogenous proteases and DNA from lysed exocrine tissue are removed. In embodiments, the filtered donor tissue may be stained with an indicator for identifying the cellular product, such as dithizone for staining islets, and examined under the microscope for the presence of intact cellular product.

The separated cellular product may not be cleanly cleaved from the donor tissue and not all of the cellular product may be completely intact. For example, with respect to islets, some islet tissue may have a diffuse or loose structure that could reflect osmotic shock due to direct immersion into an aqueous medium during any warming of a frozen pancreas. In embodiments, such a problem may be averted by employing osmotic buffering during elution of the CPA from the islet tissue during or after thawing of a frozen pancreas. Utilizing the osmotic buffering technique in embodiments may protect the structure of the islet tissue and minimize osmotic swelling and lysis during efflux of the permeating CPA. In contrast, in such embodiments, osmotic buffering does not impact the simultaneous destruction and lysis of the acinar cells because these cells have not been protected by CPA permeation.

In embodiments, sufficiently clean cleavage of islet tissue may be obtained by a cryoisolation method, in embodiments, in combination with a mild enzyme digestion to purify the islet tissue. Another approach may be to use tissue culture as a modality for the "clean-up" process since the residual acinar tissue injured during the cryo-isolation process will die and disintegrate in culture.

Examples are set forth hereinbelow and are illustrative of different compositions and conditions that can be utilized in practicing embodiments. All proportions are by weight unless otherwise indicated. It will be apparent, however, that the disclosure can be practiced with many types of compositions and can have many different uses in accordance with the disclosure above and as pointed out hereinafter. For example, these Examples will be readily recognized by those having ordinary skill in the art as also being applicable to isolating human islets because pig pancreas is an art-recognized model for human pancreas.

Pig pancreas is a useful model for at least the following reasons: (1) pig pancreas is a large animal model, (2) pigs are regarded as the most promising source of islets for future clinical xenografting. For example, in view of the current resurgence of clinical interest in hypothermic perfusion preservation of organs for transplantation, the pig provides the model of choice for large-animal preclinical evaluation of hypothermic machine perfusion (HMP) technology for segmental donor pancreas preservation. Secondly, the special case of pancreas preservation prior to islet isolation is of high significance in view of both the worldwide interest in islet xenotransplantation and our data that HMP can facilitate improved islet yields without compromising islet function.

Moreover, the consensus strategic plans recently published by the International Xenotransplantation Association for considering clinical trials of porcine islet products for type 1 diabetes emphasizes the need and importance of sterile, disease free environment for the source pigs and the products. To this end, the LifePort® system provides a convenient sterile environment for transport of the source pancreas from the site of procurement to the islet processing facility. This approach is applied to the preservation and procurement of viable islets after hypothermic perfusion preservation of porcine pancreata because pigs are now considered the donor species of choice for xenogeneic islet transplantation for a number of compelling reasons (O'Neil, J. J. et al., The isolation and function of porcine islets from market weight pigs, Cell Transplant. 10:235-246; 2001).

The age of the donor pig has proved to be a significant factor in the islet isolation process with young, socalled market size pigs (<6 months old), proving to be particularly difficult as a source of transplantable islets (7,10,50). Nevertheless, despite these challenges young pigs are favored over retired breeders (>2 years old) due to their abundance, lower animal and husbandry costs, and are more suitable to meet regulatory guidelines for donor tissue for xenotransplantation. The following examples demonstrate the efficacy of hypothermic machine perfusion of pancreata from young pigs prior to islet isolation. Data regarding the details of the surgical model that was developed in light of special considerations to achieve uniform perfusion of the porcine pancreas during 24 h of hypothermic perfusion at 7° C. are also presented.

The success of porcine pancreas hypothermic perfusion for islets isolation may strongly be influenced by the surgical procedure of organ procurement and pancreas cannulation for ex-vivo machine preservation. The development of porcine pancreas surgical recovery method has not been an obvious procedure. Initially, the lack of detailed pig pancreas anatomy documentation has led to improper organ vasculature preservation during pancreas procurement. Inadequate organ procurement has resulted in inconsistent and incomplete pancreas machine perfusion, thus low islet yield and viability.

Until recently, the anatomy of the pig pancreas was not well documented. Physiologically and topographically the pig and human pancreata are considered similar. The pancreas is an elongated retroperitoneal gland as shown in FIG. 1. In both pigs and humans, the pancreas head is closely related to the proximal duodenum, but for pigs the pancreatic duct opening is found on the duodenum distal and separate from the common bile duct (Swindle, M. M.; Smith, A. C. Comparative anatomy and physiology of the pig. Scand. J. Lab. Anim. Surg. 23:1-10; 1997). There are a variable number of vessels originating from the splenic, hepatic, gastroduodenal, superior mesenteric, and celiac arteries that on an individual basis have irregular configuration of blood supply to the pancreas. Commonly, blood to the head is supplied by the posterior and anterior arcades arising from the gastroduodenal and superior mesenteric arteries (FIG. 1). In pigs, the head does not surround the pancreaticoduodenal arteries and veins—the latter lie between the head and duodenum with the branches to the pancreas easily identifiable. The neck and the body of the pancreas are usually vascularized by the dorsal and inferior pancreatic arteries. The former can originate from the either the splenic, hepatic, or directly from the celiac arteries. The inferior pancreatic artery may begin from the superior mesenteric artery (SMA) under the neck of the pancreas and course toward the tail along the posterior inferior margin of the pancreatic surface in intimate contact with the gland. It can communicate with a varying number of splenic artery branches. The neck of the pancreas is also the site of the portal vein at the confluence of the splenic and superior mesenteric veins. The pancreas tail receives its blood supply mainly from the splenic artery.

In preparation for attaching the pancreas to the LifePort® perfusion machine, all exposed arterial branches on the margin of gastroduodenal and hepatic sides of the pancreas were meticulously identified and ligated to ensure uniform perfusion throughout the gland and allow the effluent to emerge only from the portal vein. This surgical approach proved optimal for pancreas perfusion/preservation for islet isolation, as described by Taylor, M. J., et al., in Hypothermic perfusion of pancreas: Emphasis on preservation prior to islet isolation. In: Lee, C. Y., ed., Organ perfusion preservation. Boston, Mass.: Artech House Publisher; 2010, which is hereby incorporated by reference in its entirety.

As described by Taylor et al., an exemplary surgical approach may include the following: 1. A team of two operators for pancreas procurement; 2. Follow surgical facility requirements for dress code and personal protection equipment; 3. Verify with the OR veterinary technician that the pig is intubated and under general anesthesia (i.e., ketamine 22 mg/kg, acepromazine 0.2 mg/kg, and atropine 0.025 mg/kg); confirm with the OR veterinary technician of pig anesthesia maintenance and proper ventilation; 4. Verify with the OR veterinary technician that all vital signs are monitored (ECG, heart rate, oxygen saturation level, body temperature, etc); 5. Verify that an electrical knife, a suction line and canisters are available. 6. Verify that the OR back field surgical table has been properly prepared (surgical instruments, lap sponges, gauze, cold saline, umbilical tape, etc.); 7. Verify that 2 L of cold Lactated Ringer's solution have been placed on ice; 8. Verify that an I.V. pole is available near the operating table and its height is appropriate for the gravity driven in-situ flushing of the organs (about 6 to about 6.5 feet); 9. Obtain permission from the OR veterinary technician to proceed with the surgery; 10. Minimize pancreas exposure to warm ischemia to 3 minutes, unless otherwise desired; 11. When permission has been granted, perform a midline incision from the xiphoid cartilage to just above the pelvis and expose the abdominal cavity; 12. Instruct the OR veterinary technician to administer heparin to the pig (about 150 U/kg), allow at least three minutes to pass before starting in-situ flushing; 13. Move and keep aside the bladder and the intestines (with the help of lap sponges) and identify the descending aorta; 14. Dissect, below the kidneys, a segment (about 3 cm) of the aorta apart from the surrounding tissue/vessels, place umbilical tape ties around the aortic segment; cut a small opening into the aorta between the two ties while the surgery assistant applies pressure on the aortic walls to prevent blood from squirting out; 15. Insert aortic cannula into the opening and tie it in place (make sure the umbilical tape tie is securely placed over the collar of the cannula); 16. Insert the two spikes of the irrigation set into the appropriate infusion ports of the two bags of Lactated Ringer solution (make sure the roller clamp is closed to prevent solution loss); 17. Hang the bags of Lactated Ringer solution on the I.V. pole and flush the irrigation set tubing to properly remove all the air; close the roller clamp; 18. Cross-clamp the inferior vena cava and the aorta above the diaphragm; 19. Connect the inlet opening of the cannula to irrigation set outflow port and open the roller clamp to initiate the gravity driven in-situ flushing; 20. Cut-open the inferior vena cava above the diaphragm, downstream from the clamp for blood outflow; 21. Immediately place plenty of ice inside the abdominal cavity around the pancreas and liver for organs maintenance/protection at low temperature; 22. Use the suction tubing and containers to collect the wash-out blood; 23. Make sure the solution flow from the bags, through the cannula into the aorta is not obstructed and that there is outflow from the inferior vena cava; 24. When empty, remove the bag of Lactated Ringer solution from the I.V. pole and hang the bag of SPS-1 solution (previously kept on ice), use only half of the SPS-1 solution volume to flush the organs; 25. Instruct the OR veterinary technician to euthanize the pig using a lethal dose of 5% sodium pentobarbital administered intravenously (accepted form of euthanasia according to the American Veterinary Medical Association Panel on Euthanasia (AVMA) guidelines) and complete in-situ flushing; 26. Transfer the second half of the SPS-1 solution bag to the pancreas transportation biohazard bag and place the latter on ice; 27. Carefully and rapidly (less than 15 minutes) proceed to expose and dissect apart the pancreas from the surrounding tissue and organs (add ice around the visceral organs as needed), make sure pancreas capsule and integrity are maintained; 28. Keep a segment of proximal duodenum (from near pylorus and inclusive of most the duodenum second descending part) attached to the pancreas head; make sure the duodenum segment includes the opening of the pancreatic duct (FIG. 1); 29. Ligate the splenic vein and artery prior to spleen detachment; 30. Keep an about 5 to about 7 cm long aortic segment attached to the pancreas for future organ cannulation; the aortic segment should include the openings of both superior mesenteric artery (SMA) and celiac trunk (CT); 31. Remove pancreas from the body, and with the aortic cannula attached, quickly wash off the blood from the pancreas outer surface using cold saline; immerse the pancreas in the SPS-1 solution inside the transportation bag; 32. Place the bag with the pancreas on ice, inside the pancreas cooler for transportation to the islet isolation laboratory.

Exemplary methodology for pancreas cannulation for machine perfusion may include the following: 1. A team of two operators is recommended for pancreas cleaning and cannulation; 2. Perform pancreas cannulation at the isolation laboratory in order to reduce static cold ischemia damage prior to machine perfusion; 3 Minimize pancreas exposure to static cold ischemia to less than 2 hour, static cold ischemic time is the time elapsed from the initiation of in-situ flushing to the beginning of machine perfusion; 4. Transfer the pancreas from the transporting cooler to the stainless steel surgical tray; place the latter on ice and dispense about 20-30 mL of SPS-1 solution from the transporting bag into the tray to help keep the pancreas moist and cold; 5. Remove the aortic cannula; clean away all miscellaneous tissue while paying attention to maintaining pancreas integrity; identify and expose the SMA and CT vessels; 6. Dissect the aortic segment at midline to expose the orifices of SMA and CT, at this point the SMA and CT orifices should be clearly seen positioned apart on the aortic cuff (1.5 cm×4 cm); 7. Place and secure in place the appropriate size seal-ring cannula, the correct size should enclose both SMA and CT orifices without obstruction and clearly allow for their visualization through the top clear wall of the cannula; 8. Test for leaks; fill a 20 cc syringe with the solution to be used for perfusion, attach the syringe to one end of the cannula, remove the air inside the cannula and cap the other end of the cannula, gently infuse the solution into the pancreas and identify any leaks from exposed vessels; 9. Meticulously identify and ligate all exposed leaking arterial branches on the margin of gastroduodenal and hepatic sides of the pancreas (use umbilical tape and/or silk ties appropriately); 10. Cannulate the pancreatic duct; remove the needle from the surflo-winged infusion set and use its tubing as the duct cannula; using the micro-surgery scissors cut an opening into the pancreatic duct at its originating location on the duodenum and insert the cannula; secure the latter in place by tie suturing it to the duodenum wall; 11. Measure and record pancreas weight (subtract cannula weight), mass (subtract cannula mass), volume, circumference, and/or buoyancy.

The identification and tight ligation of all exposed vessels on the hepatic and gastroduodenal sides of the pancreas are of high importance. Usually about 12 to about 14 vessels are tied prior to perfusion to eliminate the possibility for a pathway of 'least resistance' for the flow throughout the organ and to allow the effluent to emerge only from the portal vein. Leaks from open exposed vessels compromise the uniformity of the organ perfusion that in turn can lead to pressure and temperature gradients across organ surface and suboptimal pancreas preservation.

Exemplary methodology for the application of pancreas machine perfusion may include the following (FIG. 6): 1. Fill up the ice container with a mixture of ice and cold water (consult LifePort™ operation manual), place the container in the transporter main enclosure; 2. Place the organ cassette inside the cassette well, install the perfusion circuit tube frame on the pump deck and close the aluminum locking arm, connect the pressure sensor to the pressure transducer; 3. Press POWER to turn On the user controls of the transporter and follow the directions of the outer display to get the transporter ready for perfusion; 4. Add 1 L of cold perfusion solution to the organ cassette; set the infusion pressure to about 10 mmHg on the control panel, verify that the ice container temperature, as indicated by the outer display, is below about 8° C.; 5. Press WASH to start the pump and circulate the perfusate throughout the circuit; make sure all the air from the circuit is removed; 6. Place the pancreas (with the duodenum attached) inside the cassette, and position the organ cannula in the cannula mount of the cradle, connect the cannula inlet port to the infusion line and open the cannula outlet port; 7. Press PRIME to remove the air from the cannula and infusion line, and then cap the cannula; the latter will stop the flow and the pump based on the detected resistance; 8. Press STOP; press INFUSE to initiate the pancreas perfusion mode, watch for the pump to begin rotating and to increase its speed until the pressure set point is reached (e.g. about 10 mm Hg); 9. Ensure real time visualization and recording of flow parameters on both outer display and data station, the perfusion parameters as displayed on the outer panel are: pressure set point (systolic pressure, mmHg), flow rate (mL/min), resistance (mmHg/(mL/min)), temperature (° C., within the insulated cold section of transporter, i.e., ice container), to read the infusion temperature (° C.) and diastolic pressure (mmHg) press the scrolling arrows on the right side of the outer display to sequentially toggle through these additional parameters; 10. Allow pancreas perfusion for the desired amount of time, such as less than about 24 h (or in the range from about 4 h to about 24 h, such as about 8 h to about 16 h), or about 24 h or more, or in the range from about 24 h to about 48 h; stop the pump and save the data file (includes the dynamics of all perfusion parameters); 11. Remove the pancreas from the cassette; measure post-perfusion pancreas weight, mass, circumference, buoyancy, volume and record it; determine the level of fluid accumulation within the organ (edema, %).

EXAMPLES

The inclusion of the duodenum segment along with the pancreas head allows for consistent perfusion. Leaks from the small vessels diverging from the pancreaticoduodenal arteries (the two loops around the head in FIG. 1, which are between the head and duodenum in a pig) may be eliminated by maintaining the vessels integrity and thus allowing for a uniform perfusion of the pancreas head and neck. Moreover, the opening of the pancreatic duct into the duodenum may be preserved. This procedure may considerably facilitate pancreatic duct cannulation, by avoiding difficulties encountered with retracted duct identification and cannulation, and preserved early duct branches. The latter may be necessary to ensure good organ distension for gland digestion and islet isolation. The identification and tight ligation of all exposed vessels on the hepatic and gastroduodenal side of the pancreas may be of high importance. Prior to perfusion it may be necessary to eliminate the possibility for a pathway of "least resistance" (by tying certain vessels) for the flow throughout the organ, which may result in inconsistent organ perfusion, pressure, and temperature gradients across organ surface and suboptimal pancreas preservation.

Figure 8:
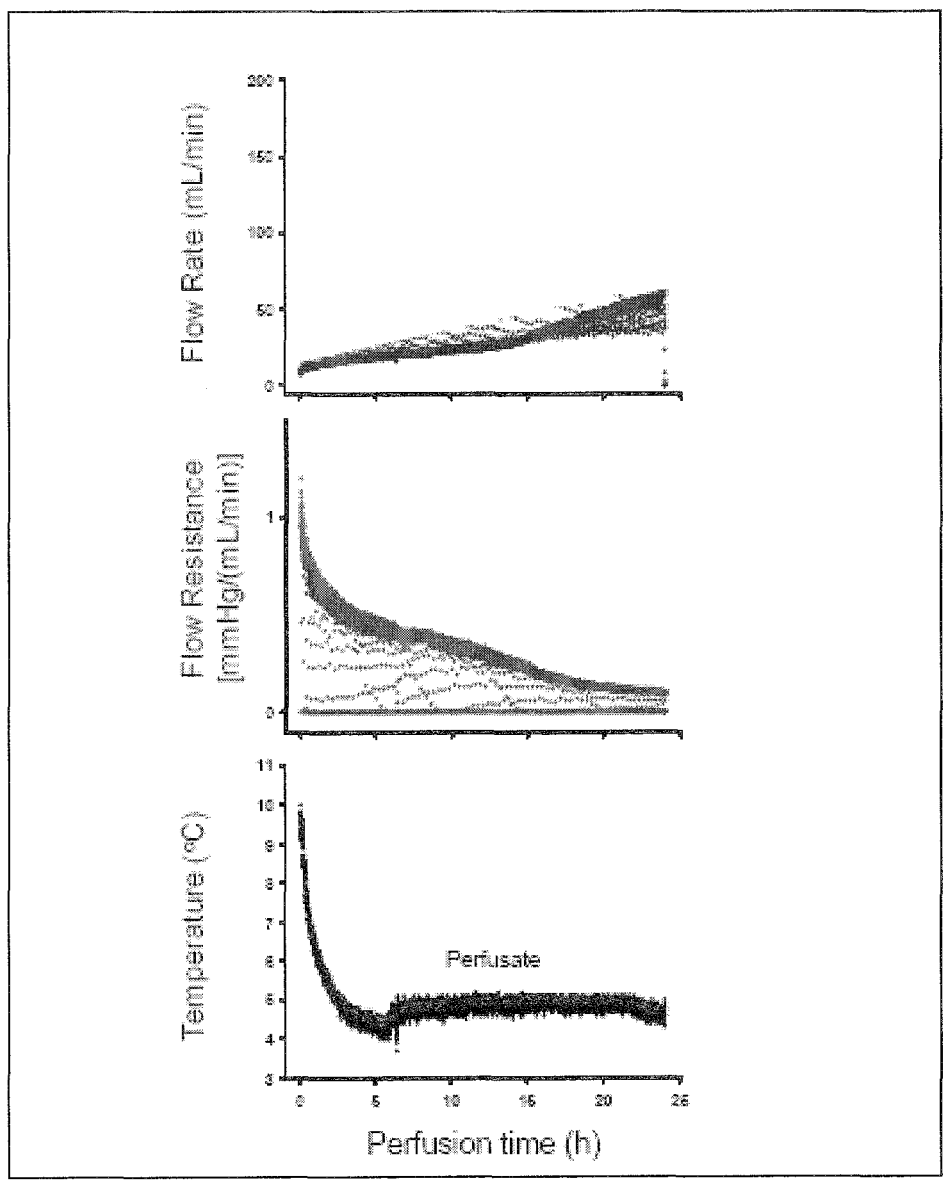
FIG. 8 is a graphical representation of exemplary pancreas perfusion parameters monitored continuously during perfusion.

Pancreas perfusion on the LifePort® may be monitored using various parameters, such as perfusion pressure (mmHg, systolic and diastolic), perfusate flow rate (ml/min), vascular resistance (mmHg/(mL/min)), and temperature (° C.). The temperatures of the perfusate and the insulated cold section of the transporter (ice container) may be measured. All these parameters may be recorded and displayed in real time by the data recording station as illustrated in FIG. 8. During perfusion each one of these parameters dynamics may be visualized and later correlated with the perfusion and/or islet isolation outcome. Hypothermic machine perfusion of young pig pancreata may performed at an infusion temperature between about 5° C. and about 7° C. The ice container is specifically designed to accommodate this temperature range through the volume of ice/water mix and the heat exchange characteristics. Also, the pump may programmed to stop if the temperature of the ice container rises above a predetermined temperature, such as about 8° C., as read by the temperature sensor located outside the container in the main enclosure and in intimate contact with container wall. Under these circumstances the preservation reverts to static cold storage for the remaining duration unless there is operator intervention to restart the pump.

A properly performed organ in-situ flushing and limited pancreas ischemia exposure prior to perfusion may result in low organ vascular resistance. The latter may be illustrated by immediate organ perfusion initiation and/or a constant reduction in vascular resistance and increase in flow rate throughout the duration of perfusion (FIG. 8). For open flow circuits, with leaking pancreata, tubing and fittings, the transporter fails to maintain the imposed infusion pressure, thus resulting in erroneous perfusion and pump inactivation. This event may be remedied by operator intervention to identify and correct any leaks responsible for the low vascular resistance status.

Materials

Surgical procurement of pig pancreas: Animal designated research surgical facility (the OR should provide adequate environment and instrumentation to ensure proper pig anesthesia, ventilation and vital signs monitoring during pancreas procurement); domestic Yorkshire male farm pigs, 25 to 32 kg; pancreas recovery cooler containing: one aortic cannula (size 18, Brad), a two spikes 'Y' irrigation set (Medline), one sterile biohazard bag, 1 L of cold UW solution (SPS-1, Organ Recovery Systems); pack cooler half way with ice for organ transportation from the OR to the isolation lab; Lactated Ringer's solution, 2 L (B Braun Medical.).

Pancreas cannulation for machine perfusion: Surgical tray and instruments (Mayo and Metzenbaum scissors, DeBakey forceps, curved and straight hemostatic forceps, microsurgery spring scissors, needle holders); gauzes (4"×4") and umbilical tape (10"segments); sterile suture, coated Vicryl, 4-0, RB-1, 17 mm, ½ c taper needle (Ethicon); sterile ties, 0 (3.5 metric) silk, black braided (Ethicon); surflo-winged infusion set, 21 G×¾", 12" tubing, V=0.45 mL (Terumo); sterile needles (16 G, 18 G) and 20 cc syringes; LIFEPORT disposable 10×35 mm and 7×20 mm sealring cannulae (Organ Recovery Systems); LIFEPORT disposable 3, 5, 8 mm straight cannulae and coupler (Organ Recovery Systems); perfusion solution, 1 L, (KPS-1, UHK, Organ Recovery Systems, Inc.); tissue weighing scale; and trays.

Pancreas machine perfusion: LifePort™ Kidney Transporter, pulsatile configuration (includes insulating cover, ice container, power and data acquisition cable, batteries, Organ Recovery Systems); organ cassette (includes vented dual leads and organ cradle with cannula mount, Organ Recovery Systems); perfusion circuit frame with built-in pressure sensor (includes filter and compliance chamber, Organ Recovery Systems); data recording station (computer and data station software).

Small farm pigs (Domestic Yorkshire, male, 25-32 kg; Hambone Farms, S.C.) were used as pancreas donors. Following induction of general anesthesia with ketamine (22 mg/kg), acepromazine (0.2 mg/kg), and atropine (0.025 mg/kg), and anesthesia maintenance with isoflurane in oxygen, the animals were intubated and connected to a ventilator. The abdominal cavity was opened through a midline incision from the xiphoid cartilage to just above the pelvis, and the descending aorta was identified and cannulated below the kidneys. The inferior vena cava and aorta were identified, isolated, and closeclamped above the diaphragm. An in situ gravity-driven flushing of the pancreas was initiated using 2 L of cold lactated Ringer's solution while for blood flow the inferior vena cava was cut open above the diaphragm, downstream from the clamp. The pig was euthanized through exsanguinations and a lethal dose of 5% sodium pentobarbital administered intravenously. The latter is an accepted form of euthanasia according to the latest guidelines from the American Veterinary Medical Association Panel on Euthanasia (AVMA). All animal care and handling complied with policies and approval of the Institutional Animal Care and Use Committee (IACUC) at the Medical University of South Carolina, where the organ procurements were carried out.

Organ exposure to warm ischemia was kept below 3 min by using the cold solution vascular flush and by placing ice inside the abdominal cavity during surgical excision of the pancreas. The pancreas was carefully and rapidly exposed and dissected apart from the surrounding tissue and organs. A segment of proximal duodenum starting near the pylorus and inclusive of most of the duodenum's second descending loop was kept intact with the pancreas to protect the superior and inferior pancreaticoduodenal arteries (FIG. 1). The common bile duct and pancreatic duct openings were included as part of the duodenum segment. This considerably facilitated pancreatic duct cannulation, by avoiding the difficulties encountered with retracted duct identification and cannulation, and preserved early duct branches. The latter were necessary to ensure good organ distension for gland digestion and islet isolation. The splenic vein and artery were ligated prior to detachment of the spleen (FIG. 1). A 5-7-cm-long aortic segment was left attached to the pancreas for future organ cannulation. The segment included the openings of both superior mesenteric artery (SMA) and celiac trunk (CT) vessels (FIG. 1). The pancreas was removed from the body, immersed in cold University of Wisconsin solution (UW; Viaspan, Fisher Scientific), and placed on ice for transportation from the operation room to the research laboratory, a trip of less than 30 min. Overall, from the initiation of in situ cold flushing to the beginning of ex vivo hypothermic perfusion, the pancreata exposure to static cold ischemia was kept below 2 h. Upon arrival at the lab all exposed arterial branches on the margin of gastroduodenal and hepatic sides of the pancreas were meticulously identified and ligated to ensure uniform perfusion throughout the gland and allow the effluent to emerge only from the portal vein by avoiding leaks from the many arterial branches.

Pancreas Cannulation and Perfusion

Due to anatomical configurations and variations of the vasculature in the pancreas from young pigs it proved difficult to achieve a consistent perfusion preparation by using direct cannulation of the SMA and celiac truck individually. This was due to arterial side branches that were easily blocked and impeded by the cannulas as illustrated in FIGS. 2A and B. This problem was circumvented by employing a seal-ring cannula (10×35 mm; Organ Recovery Systems), which has a geometric design that permitted direct access to the openings of the SMA and CT via an aortic patch as illustrated in FIG. 2C.

Figure 6:
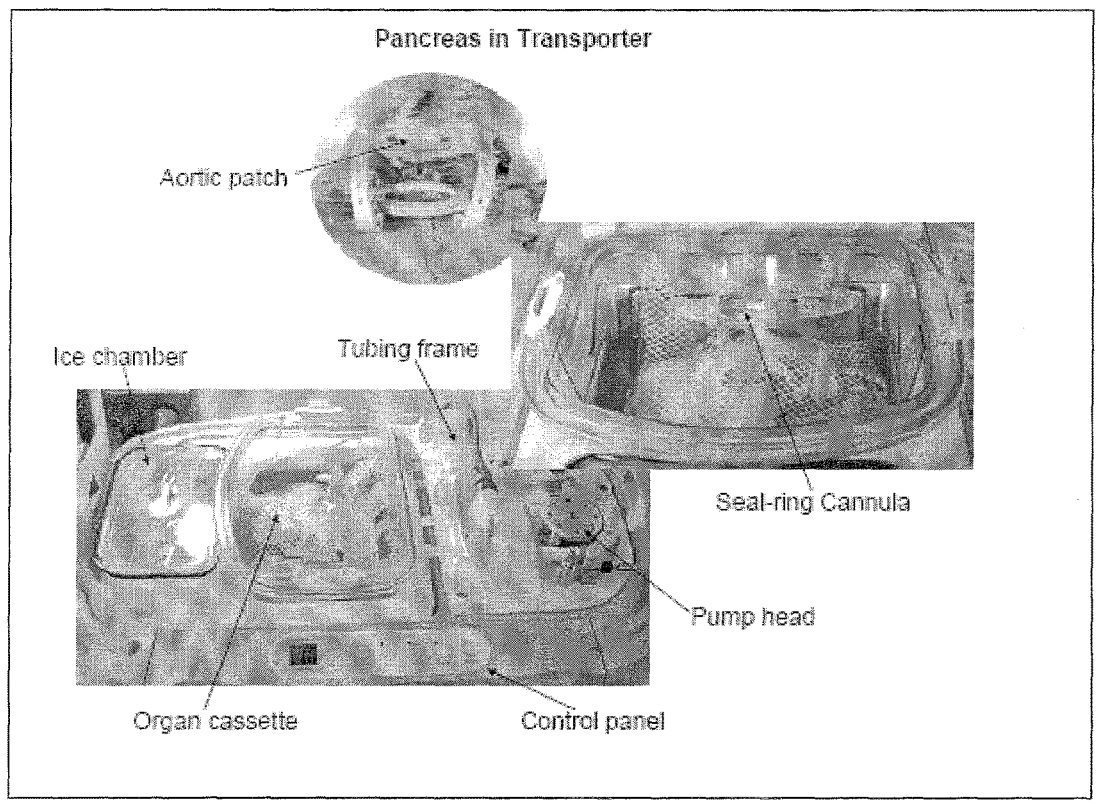
FIG. 6 are photographs illustrating hypothermic perfusion preservation of a porcine pancreas on a LifePort® machine; the lower panel shows the principal features of the LifePort®; the middle panel shows the details of a pig pancreas installed in the perfusion cassette and hooked up to the perfusion inlet line via a seal-ring cannula; this proprietary cannula allows simultaneous perfusion of the celiac trunk (CT) and superior mesenteric artery (SMA) by way of an aortic patch clamped in the seal-ring cannula (see circular inset); the inset photo shows the opening of the CT and SMA in the aortic patch (AP) which was exposed for viewing by opening the seal-ring cannula.

For the porcine pancreas, all flow problems are eliminated by using the seal ring cannula for perfusion. Its geometrical design allows for direct flow to the pancreas CT and SMA vessels without interference. The cannula is placed on the aortic patch inclusive of the two vessel openings, without obstructing the vessels as illustrated in FIG. 6 and FIG. 9a. This contrasts with the use of insertion cannulas that enter the arterial lumen and potentially impede or occlude the openings to vascular side branches. The seal-ring cannula provides a sealed flow link between the pancreas and perfusion system and ensures 24 hour continuous uniform perfusion without undesirable events.

The LifePort® perfusion machine provided a controlled closed loop pulsatile perfusion at a set systolic pressure of 10 mmHg. In order to hook up the pancreas to this machine for consistent 24-h uninterrupted perfusion, several methods of cannulation were evaluated. Initially, a 5-7-cm-long aortic segment, inclusive of both the superior mesenteric artery (SMA) and celiac trunk (CT) arterial openings, was used by ligating one end of the aortic segment and inserting a straight cannula (6.25 mm OD connector) into the other end. The cannula was attached to the infusion port of the LifePort® pump. However, this arrangement proved to be problematic due to the configuration of the clinical LifePort® machine, which was unable to reach and maintain the target perfusion pressure.

For the aortic cannulation, a 5-7 cm long aortic segment, inclusive of both superior mesenteric and celiac trunk artery openings, is ligated at one end and straight-cannulated (6.25 mm OD cannula) at the other end. The cannulated end is attached to the pump infusion port. Under this configuration, possibly due to aortic segment elasticity, the pump was unable to reach or sustain its targeted perfusion pressure. By design, under these circumstances the LifePort® is configured to try to compensate by increasing its speed until the maximum allowed value is reached (240 mL/min), thereafter the pump stops. These conditions of increased pump speed inevitably result in higher fluid accumulation in the tissue as reflected in a doubling of the glandular edema. At this point, usually within 6-12 hour from perfusion onset, the pump stops and the organ preservation reverts to conventional cold static storage by fluid immersion only without circulating perfusate. It is presumed that the inherent compliance in the aortic segment relative to the vascular resistance of the pancreas contributed to this phenomenon.

Figure 2:
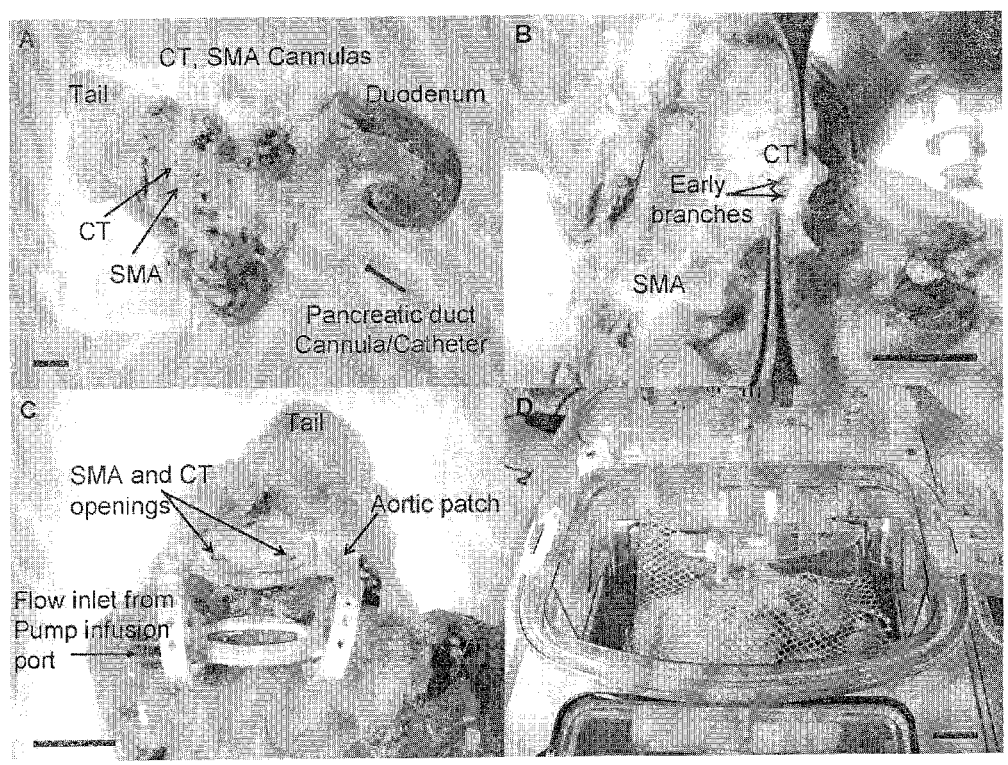
FIGS. 2A-D are photographs depicting the cannulation of an excised pig pancreas, (A) excised pig pancreas with attached duodenal section to preserve the superior and inferior pancreaticoduodenal arteries, (B) cut-down arterial vessel (CT) illustrating early side branches that may be occluded when straight cannulas; (C) illustrates the openings of the CT and SMA on an aortic patch clamped inside the seal-ring cannula, (D) a pig pancreas immersed in perfusion solution in an organ cassette and perfused via a seal-ring cannula installed on the LifePort® perfusion machine, the scale bar in each panel is 2 cm.

Alternative modes of cannulation were evaluated involving direct straight cannulation of the SMA and celiac trunk individually using two 4 mm OD luer-to-barb connectors joined together with a coupler attached to the pump infusion port (FIG. 2). The success of this arrangement proved to be dependent on anatomical differences from one pig pancreas to another. Specifically, increased flow resistance and eventual pump stalling with incomplete perfusion is problematic and may occur due to occlusion of arterial side branches by the cannulas inserted into the SMA and CT as illustrated in FIG. 2, which occurred in about one third of the cases. These flow problems were alleviated by using a proprietary seal ring cannula (10×35 mm; Organ Recovery Systems) illustrated in FIG. 2C. These cannulas are designed to enclose the openings of the SMA and CT by clamping an aortic patch as shown in FIG. 2C. In this way it provided a sealed flow link between the pancreas and the perfusion system without compromising the normal physiological flow even if early side branches were present. These constraints may be peculiar to the anatomy of juvenile pigs but the use of the seal ring cannula permitted consistent, trouble-free perfusion for about 24 h, and even about 48 h.

Using the straight-cannulation insertion method, the CT and SMA vessels are individually cannulated with 4 mm OD luer-to-barb connectors that are directly inserted inside the two vessels (FIG. 9c). The two connectors/cannulae are joined together with either a coupler (FIG. 10), or a "T" connector (FIG. 9c). The latter is attached to the pump infusion port. In the case of young pig pancreata, this approach is dependent on organ anatomy, and in many cases has provided inconsistent perfusion and increased flow resistance that ultimately leads to flow ending, pump stopping and incomplete organ perfusion for reasons that will now be discussed. In young pig pancreata, several small vascular branches diverge early from both the celiac trunk and superior mesenteric artery and can be blocked by the cannula tip (illustrated in FIG. 11). Although the cannula is normally advanced only 6 mm inside the vessels (20 mm long), obstructing the flow from the cannula to the branches leads to none, or differential perfusion across the organ surface. In marked contrast, straight-cannulation of the SMA and splenic artery of human pancreata is a simple, basic procedure that is not subject to the same anatomical constraints as the porcine pancreas. As for the porcine pancreas, the two cannulae are connected with a coupler that in turn is attached to the transporter infusion port (see FIG. 10). The human pancreas may also perfused with the duodenal segment attached. The diameter of the straight cannulae vary according to human pancreas size and anatomy, normally they cover the range of from about 3 to about 10 mm.

The LifePort® pulsatile system was initially designed, and FDA cleared, for kidney hypothermic perfusion/preservation for clinical transplantation (Baicu, S. C. et al., Interstitial fluid analysis for assessment of organ function, Clin. Transplant. 18, Suppl. 12:16-21; 2004; Baicu, S. C., The role of preservation solution on acid-base regulation during machine perfusion of kidneys, Clin. Transplant. 20:113-121, 2006; and Moers, C. et al., Machine perfusion or cold storage in deceased-donor kidney transplantation. N. Engl. J. Med. 360:7-19; 2009). Using the kidney system the pancreas was perfused in a closed loop while being completely immersed in the perfusion solution inside the organ cassette, which comfortably accommodated the whole pancreas from these young pigs (FIG. 2D). The cassette also served as a solution reservoir, the perfusate being drawn out by the pump, was passed through the filter, bubble trap, the infusion port before returning to the pancreas and organ cassette. Pancreas submersion in the temperature controlled perfusate helped eliminate temperature gradients across the organ surface and ensure high-quality hypothermic preservation. The selected perfusate (1 L) was maintained at 5-7° C. A pulsatile (30 pulses/min) constant low pressure flow regime was imposed with a setting of 10 mmHg for the systolic pressure. The perfusion pressure value of 10 mmHg was selected based on the fact that physiologically the pancreas is a low flow organ and all preliminary experiments performed to optimize the perfusion regime of juvenile pancreata indicated a need for either low pressure, or low flow rate, driven perfusion preservation. The technical features of the already commercially available LifePort® system were able to support these demands. Perfusion flow rate and pressure, organ resistance, and perfusate temperature were measured, recorded, and displayed in real time. Organ weight was measured before and after perfusion and used to determine postpreservation fluid accumulation within the organ (edema). More details of the development of the method of perfusion for the pancreas are described in Taylor, M. J., et al., Hypothermic perfusion of pancreas: Emphasis on preservation prior to islet isolation. In: Lee, C. Y., ed., Organ perfusion preservation. Boston, Mass.: Artech House Publisher, 2010, the disclosure of which is hereby incorporated by reference in its entirety.

Pancreas Distension and Islet Isolation Islets were isolated from fresh and hypothermically preserved pancreata. Following either organ recovery or preservation, dissociation enzyme (Liberase PI, Roche, Indianapolis, Ind.) was delivered to the pancreas via the pancreatic duct by direct syringe infusion. Prior to its and use the Liberase (0.5 g) was reconstituted to a final volume of 350 ml with HBSS (Hank's balanced salt solution, VWR, Suwanee, Ga.) and permanently maintained on ice. Three different batches of Liberase PI were employed throughout the duration of the experiments reported here. The average value of collagenase activity for the three lots was 2192.4±114.6 Wunschs per vial (500 mg) with a standard deviation of 198.6 Wunsch. Following intraductal pancreas distension, all extraneous tissue was removed and the pancreas was cut in seven to nine pieces. The latter were placed in a 1000 ml Ricordi chamber (BioRep Technologies Inc., Miami, Fla.) containing of nine stainless steel balls and a 500-μm mesh screen.

The dissociation chamber, an integral part of the Ricordi islet dissociation system (a 1200-ml pump driven temperature controlled flow circuit), was already primed (RPMI, Invitrogen, Carlsbad, Calif.) and brought to physiologic temperature (36±1° C.). Through combined chamber mechanical agitation and enzymatic digestion the islets were liberated under controlled conditions of temperature and flow rate. With the aid of dithizone staining, periodic sampling of the tissue digest allowed visualization under the microscope of the progress of tissue digestion and the percentage of free islets, and guided the assessment of digestion end point. When the digestion end point was determined, the digestion was stopped and the dilution phase (with 4 L of cold RPMI) was initiated while the tissue digest containing free islets was collected and placed on ice. The tissue digest was washed three times (3 min, at 4° C. and 1000 rpm) with cold 10% FCSHBSS, and the final tissue/islet pellet was consolidated in two 250-ml conical tubes. The packed cell volume was weighed and recorded (less than 20 g/tube), the islet pellet was resuspended in UW, up to 100 ml per tube, and placed on ice for a cold incubation of at least 30 min. Periodic swirling of tubes was performed to avoid pellet compaction.

Islet Purification

At the completion of cold incubation in UW solution, islet purification based on density gradient centrifugation was performed using the COBE 2991 (Gambro BCT, Lakewood, Colo.). A continuous Ficoll gradient of 1.108 and 1.069 densities was employed to separate the cells at 2400 rpm for 5 min. The purified Ficoll islet fractions were collected sequentially in six predetermined 250 ml conical tubes (prefilled with 2.5% FCS-M199 media). The remaining content of purification bag was also retrieved in the seventh tube. All tubes were centrifuged at 4° C. and 1500 rpm for 3 min. Following appropriate supernatant removal, the fractions were sampled (0.5 ml sample in 2 ml of dithizone solution) to determine under the microscope the purest fractions. Dithizone solution (50 mg diphenylthiocarbazone and 5 ml dimethyl sulfoxide in 45 ml phosphate buffer solution) was used to stain the islets for their identification and quantification. Images of all fractions were recorded for comparison purposes. The fractions containing islets were recombined as found appropriate, properly labeled, and assigned for islet counting and/or viability testing.

Islet Quantification and Assessment

Following islet isolation and purification the total number of islets was determined using conventional techniques (for example, see Ricordi, C. et al., Pancreatic islet cell transplantation. Austin, Tex.: R. G. Landes; 1992:132-142). Briefly, a volume of 100 µl of islet fraction was placed in 250 µl of dithizone solution inside a 35×10 mm tissue dish with grid. Thus, islets were stained, counted, and converted to islet equivalents (IE) according to standard convention. Counts were performed in duplicate by two independent observers. The purity of the islet preparation was also assessed by comparing dithizone-stained tissue to unstained exocrine tissue.

Islet Insulin Content and Stimulated Secretion Assay

Islet insulin release upon exposure to low and high glucose concentrations was determined following an initial recovery of 1 h at 37° C. in low (2 mM) glucose (in RPMI-1640) solution. Then consecutive 30-min islet incubation periods (37° C. water bath shaker) in 2, 20, and 2 mM glucose solution, respectively, were performed, each followed by supernatant removal and freezing (0.5 ml), and islet resuspension in the next glucose concentration solution. The insulin content and glucose stimulated insulin response assessments were carried out immediately following islet purification and quantification, without prior incubation/culturing. Based on the purest fraction(s) islet yield, small volume aliquots of islet suspension containing 25 IE were distributed to each one of the 12×1.5 ml conical tubes containing 1 ml of the corresponding glucose solution. Gravity driven sedimentation of islets within the 1.5-ml conical tubes was used prior to removal of supernatant (0.5 ml per tube) at the end of each glucose stimulation phase.

From the purest fraction(s) islet suspension, two samples of 0.5 ml were removed and subsequently frozen to later determine the insulin and amylase content, respectively. The insulin release upon glucose stimulation of the frozen supernatants and the insulin content of the purest fraction(s) samples were quantitatively determined using the Insulin Porcine EIA kits (Alpco Diagnostics, Windham, N.H.). The latter is a solid phase two-site enzyme immunoassay based on the direct sandwich technique. According to manufacturer's protocol, two monoclonal antibodies are directed against separate antigenic determinants on the insulin molecule, the bound enzyme labeled antibody to the insulin molecule is detected by a reaction with the 3,3',5,5'-tetramethylbenzidine and the end point is read spectrophotometrically (Spectra Max Plus 384; Molecular Devices, 450 nm). The results were normalized to islet equivalent and expressed as ng/ml/IE. The EnzChek Ultra Amylase Assay kit (Molecular Probes, Carlsbad, Calif.) was used to measure the amylase content, as per manufacturer's specifications.

Islet Viability

Glutathione and ATP were measured as indices of tissue injury and energy status, respectively. For this, from the purest fraction(s) islet suspension samples were removed, 1 and 0.5 ml for glutathione and ATP measurements, respectively, spun and immediately immersed in liquid nitrogen after complete supernatant removal. These two volumes satisfy the analysis requirements for the two assays employed for glutathione and ATP quantification using the Glutathione Fluorimetric Assay kit (Sigma, St. Louis, Mo.) and Viability-ATP Assay kit (Dojindo Molecular Technologies, Gaithersburg, Md.), respectively. The sample analysis was performed in accordance with the manufacturer's assay instructions; glutathione and ATP were determined, normalized to IE and expressed in nM/IE.

Structural Analysis

A protocol for pancreas tissue processing was developed to visualize morphological changes induced by the organ preservation methods. In this protocol, all wedge biopsies were fixed overnight in 2% glutaraldehyde/0.1 M Sorenson's buffer solution. Following this, the samples were rinsed (0.1 M Sorenson's buffer) and placed in 2% Osmium/0.1 M Sorenson's buffer solution for 1 h. After another rinsing the samples were dehydrated using a graded series of acetone solution and infiltrated with Araldite 502 resin using initially a 1:1 resin/acetone mixture. After 30 min the samples were moved to a 9:1 resin/acetone mixture, placed on a vertical rotator, and left overnight. The next day, the samples were transferred to 100% resin containing molds ensuring no air bubbles were present and polymerized at 60° C. for 24 h. Thick sections (2 µm) were cut using an ultramicrotome, stained with toluidine blue, and viewed with the aid of a light microscope.

The following data demonstrate the effects of both the nature of the perfusate and prior warm ischemia on islet isolation from juvenile pig pancreases. The experimental groups in relation to the conditions of preservation are summarized in Table 1.

TABLE 1

Experimental Groups

| Group | Storage Condition | Warm Ischemia Time | Cold Ischemia Time | N |
|---|---|---|---|---|
| 1. Fresh control | None | 0 | <2 h | 7 |
| 2. Static cold storage | Static cold storage, 2-4° C. after flush with UW-Viaspan | 0 | 24 h | 9 |
| 3. Hypothermic machine perfusion | Machine perfusion with KPS1 or UNISOL, pressure = mmHg, temperature = 5-7° C. | 0 | 24 h | 7 |
| 4. Hypothermic machine perfusion | Machine perfusion with KPS1 or UNISOL, pressure = 10 mmHg, temperature = 5-7° C. | 30 min | 24 h | 7 |

Preservation Solutions

Three solutions were used for pancreas hypothermic preservation: (i) UW (Viaspan, Ban), for static cold storage; (ii) KPS-1 (Organ Recovery Systems), FDA cleared for kidney machine perfusion; and (iii) UNISOL-UHK, part of the Unisol™ proprietary family of solutions (Organ Recovery Systems and Cell and Tissue Systems, Charleston, S.C.) (See U.S. Pat. No. 6,492,103). Currently Viaspan, considered the "gold standard" solution for organs hypothermic preservation, is the most commonly used solution in clinical organ transplantation. KPS-1, a hybrid "intracellular/extracellular" solution, is the current industry standard for machine perfusion of kidneys (23; Szust, J. et al., A comparison of OPO pulsatile machine preservation practices and results. J. Transpl. Coord. 9:97-100, 1999).

The Unisol™ family of solutions, of which UNISOL-UHK is a component, has been designed as a universal solution system for optimum cell, tissue, and organ preservation. UHK, the Unisol™ intracellular base solution, was designed for application at profound hypothermic temperatures (<15° C.). Table 2 shows the chemical formulations for the solutions used in this application. The UHK solution, prior to its use, was supplemented with fresh reduced glutathione (3 mM), in accordance with its chemical formulation (Baicu, S. C. et al., The role of preservation solution on acid-base regulation during machine perfusion of kidneys, Clin. Transplant. 20:113-121, 2006; Baicu, S. C. et al, Modulating biochemical perturbations during 72-hour machine perfusion of kidneys: Role of preservation solution, Cryobiology, 54:114-120, 2007; U.S. Pat. No. 6,492,103; Taylor, M. J., Biology of cell survival in the cold: The basis for biopreservation of tissues and organs. In: Baust, J. G., Baust, J. M., eds., Advances in biopreservation, Boca Raton, La.: CRC Press, 2007:15-62; Taylor, M. J. et al., Design of Preservation Solutions for Universal Tissue Preservation in vivo: Demonstration of efficacy in pre-clinical models of profound hypothermic cardiac arrest. Transpl. Proc. 37: 303-307, 2005; the disclosures of which are hereby incorporated by reference in their entireties). KPS-1 solution contains the same amount of glutathione, but was added at the time of solution manufacture.

TABLE 2

Preservation Solution Formulations

| Chemical Components (mM) | UW (Viaspan) | KPS-1 (Belzer-MPS) | UHK (Unisol™-I base) |
|---|---|---|---|
| Ionic | | | |
| Na$^+$ | 30.0 | 100.0 | 62.5 |
| K$^+$ | 125.0 | 25.0 | 70.0 |
| CA$^{2+}$ | — | 0.5 | 0.05 |
| Mg$^{2+}$ | 5.0 | 5.0 | 15.0 |
| Cl | — | 1.0 | 30.1 |
| So$_4$ | 5.0 | — | — |
| PH Buffers | | | |
| H$_s$PO$^-_4$ | 25.0 | 25.0 | 2.5 |
| HCO$^-_3$ | — | — | 5.0 |
| HEPES | — | 10.0 | 35.0 |
| Impermeants | | | |
| Lactobionate$^-$ | 100.0 | — | 30.0 |
| Raffinose | 30.0 | — | — |
| Sucrose | — | — | — |
| Mannitol | — | 30.0 | 25.0 |
| Glucose | — | 10.0 | 25.0 |
| Gluconate | — | 85.0 | 70.0 |
| Ribose | — | 0.5 | — |
| Adenosine | 5.0 | — | 2.0 |
| Colloids | | | |
| HES | 5% | 5% | — |
| Dextran 40 | — | — | 6% |
| Osmolality (mOsm/kg) | 320 | 300 | 350 |

Each pancreas was assigned to one of six preservation treatment groups: fresh controls—processed immediately (cold ischemia <1 h) (G1, n=7); static cold storage—flushed with cold UV-Viaspan and stored in UV-Viaspan at 2-4° C. for 24 h with no prior WIT (G2, n=9); HMP perfused on a LifePort® machine at 4-6° C. and low pressure (10 mmHg) for 24 h with either KPS1 solution (G3, n=7) or UNISOL-UHK (G4, n=7). Additional treatment groups to evaluate the effects of prior warm ischemia examined islet isolation after 30 min WIT in situ without (G5, n=6) or with subsequent 24-h HMP with KPS1 (G6, n=7). The pancreas was intraductally distended with Liberase PI enzyme and normothermically digested. The isolated islets were purified by a continuous density-gradient centrifugation. Perfusion-induced glandular edema was G3=138±19%, G4=160±16%, and G6=127±22%. Islet yield (IEQ/g of pancreas) varied between the groups: G1=1,425 ±610, G2=1,002±262, G3=2,242±449 (p<0.05 vs. G2), G4=1,901±420 (p<0.05 vs. G2), G5=1,756±329, and G6=1,396±243.

The method of preservation had a significant impact on the extent of digestion time and the amount of free islets released from the pancreatic digest. Data are summarized in Table 3 and illustrated in FIG. 3. Microscopic examination of the different preparations using dithizone staining for islets showed a consistently more uniform digestion of the pancreata from G3 and G4 compared with G1 and G2, with greater separation of the tissue and less entrapped islets (FIG. 4). Tissue digest from both fresh (G1) and SCS control group (G2) pancreata showed more mantled (incompletely cleaved islets with adherent exocrine tissue) and entrapped islets (FIG. 4A-D) in comparison to perfused organs (FIGS. 4E and F). Islet sampling during the process of digestion revealed early free islets and a more homogenous digest, without fragments of exocrine tissue, for the machine perfused pancreata (FIG. 4E). The islet retrieval data are summarized in FIG. 3, which shows that pancreas perfusion, resulted in a high yield of islets that was statistically significantly (p<0.05) when compared to the experimental control cold flush group (G2). Machine perfusion allowed the remnant blood to be washed out and also, based on the amount of water accumulation (edema), provided a disrupted extracellular space without a negative impact on the ductal distension. These ultimately helped rapidly free more islets and a correlation between edema and digestion time exists with shorter digestion times in pancreases with higher edema (Table 3). The slightly negative edema observed in the cold flush group (−2.8±0.7%) appears to have been due to the hypertonicity of the UWViaspan solution.

perfused pancreata while it contained entrapped islets from control and fresh organs (FIG. 4B, right). The purity of the islet preparations after density gradient purification, measured as the ratio of insulin (from islets) to amylase (from exocrine cells), was also increased in the perfused groups compared with both fresh and static cold storage (Table 3). The size distribution of the islets harvested in the different groups is summarized in Table 4, which shows that a very high percentage (>90%) of the islets harvested from preserved pancreases was in the range 50-100 μm irrespective of the mode of preservation. This was not significantly

TABLE 3

Pancreas Preservation and Islet Isolation Indices

| Pancreas/Islet Characteristics | G1: Fresh (Untreated Control, N = 7) | G2: Control (Viaspan, N = 9) | G3: HMP (KPS-1, N = 7) | G4: HMP (UHK, N = 7) | G5: 30WIT N = 6 | G6 30WIT/HMP (KPS-1, N = 7) |
|---|---|---|---|---|---|---|
| Postpreservation edema (%) | — | −2.8 ± 0.7 | 138 ± 19 | 106 ± 16 | — | 127 ± 21 |
| Pancreas weight at procurement (g) | 115 ± 7 | 118 ± 5 | 107 ± 8 | 103 ± 3 | 111 ± 2 | 110 ± 6 |
| Undigested tissue (%) | 17.8 ± 2.9 | 21.9 ± 3.2 ®† | 29.4 ± 4.5 | 28.3 ± 3.3 | 28.6 ± 2.2 | 24.2 ± 2.7 |
| Digestion time (s) | 757 ± 61 | 707 ± 39 | 638 ± 27 | 553 ± 23‡ | 335 ± 30§ | 426 ± 18¶ |
| Insulin stimulation index | 4.59 ± 1.33 | 2.45 ± 0.37 | 2.88 ± 0.44 | 3.26 ± 0.34 | 6.21 ± 2.18 | 4.17 ± 0.43 |
| High-glucose insulin (ng/multilayerIE) | 0.33 ± 0.15 | 0.20 ± 0.05 | 0.23 ± 0.08 | 0.27 ± 0.03 | 0.22 ± 0.02 | 0.36 ± 0.05 |
| Insulin content (ng/IE) | 4.25 ± 1.84 | 2.37 ± 0.5 | 5.9 ± 1.89# | 5.02 ± 1.02 | 2.70 ± 0.38 | 3.28 ± 0.53 |
| Amylase content (μg) | 51.06 ± 29.55 | 6.60 ± 1.07 | 14.1 ± 3.67 | 22.21 ± 6.40 | 2.95 ± 0.72 | 9.26 ± 3.39 |
| Insulin/amylase (%) | 4.71 ± 1.13** | 11.54 ± 1.89 | 25.53 ± 5.02 | 25.49 ± 8.02 | 74.92 ± 22.72 | 16.24 ± 4.3 |

*N = 4.
†N = 6.
†‡p < 0.05 versus G1, G2 (Anova, Tukey's posttest).
§p < 0.01 versus G1, G2, G3, G4 (ANOVA, Tukeys' posttest)
¶p < 0.01 versus G1, G2, G3 (ANOVA, Tukey's posttest).
p < 0.05 versus G2.
**p < 0.01 versus G2-G6.

Following purification, for all the experimental groups, the purified islets were found in two fractions; frequently one fraction had more islets than the other one, which often contained bigger islets and less exocrine tissue. The fractions were labeled chronologically, in the order of collection, from 1 to 7. Most of the free pure islets in the preps from perfused pancreata, with or without 30 min of warm ischemia exposure (G3, G4, G6), were found in fractions 3 and 4. The purest islets of static stored pancreata (G2) and nonpumped warm ischemic (30 min) organs (G5) were usually seen in fractions 2 and 3. However, in the case of fresh and Viaspan control group pancreata, free islets were also contained by fractions 5 and 6, for these group pancreata the prep revealed entrapped islets within exocrine tissue fragments that were unable to migrate in the density gradient.

In the HMP group, where significantly shorter digestion times were needed and more uniform preps of separated islets and exocrine tissue were seen, a density gradient separation was more efficient, with a higher yield and purity of islets (see FIG. 4). Fraction 7, which contained the remnants from the density gradient bag, had no islets for different (ANOVA) to the size distribution obtained from control untreated pancreases obtained from these young pigs. The islet counts given in Table 4 represent the yield expressed as absolute islet numbers irrespective of their size (>50 μm) and is distinct from the yields shown in FIG. 3, which are expressed in terms of "islet equivalents" using the standard convention (34). The size distribution of islets obtained from these juvenile pigs concurs with previous reports in the literature comparing adult and young porcine donors (Dufrane, D. et. al., Impact of porcine islet size on cellular structure and engraftment after transplantation: Adult versus young pigs. Pancreas 30:138-147, 2005; Jay, T. R., et al., The distribution of porcine pancreatic betacells at ages 5, 12 and 24 weeks. Xenotransplantation 6:131-140, 1999; Jay, T. R., The distribution of porcine pancreatic betacells at ages 5, 12 and 24 weeks. Xenotransplantation 6:131-140, 1999; Toso, C. et al., Isolation of adult porcine islets of Langerhans. Cell Transplant., 9:297-305, 2000; Ulrichs, K. et al., Histomorphological characteristics of the porcine pancreas as a basis for the isolation of islets of langerhans. Xenotransplantation 2:176-187, 1995).

TABLE 4

Islet Size Distribution

| Group | N | Total Islet Count (×1,000) | Islet Size Range 50-100 μm (%) | Islet Size Range 101-150 μm (%) | Islet Size Range 151-200 μm (%) | Islet Size Range >200 μm (%) |
|---|---|---|---|---|---|---|
| G1. Fresh control | 7 | 1,220 ± 450 | 89.0 ± 2.4 | 9.4 ± 1.6 | 1.2 ± 0.7 | 0.3 ± 0.2 |
| G2. SCS (UW) | 9 | 577 ± 152 | 91.8 ± 1.8 | 7.6 ± 1.7 | 0.6 ± 0.2 | 0.04 ± 0.04 |
| G3. HMP-KPS1 | 7 | 825 ± 188 | 90.9 ± 1.0 | 8.5 ± 1.0 | 0.6 ± 0.2 | 0.03 ± 0.03 |

TABLE 4-continued

Islet Size Distribution

| Group | N | Total Islet Count (×1,000) | Islet Size Range 50-100 μm (%) | Islet Size Range 101-150 μm (%) | Islet Size Range 151-200 μm (%) | Islet Size Range >200 μm (%) |
|---|---|---|---|---|---|---|
| G4. HMP-UHK | 7 | 848 ± 176 | 96.0 ± 0.5 | 3.7 ± 0.5 | 0.3 ± 0.1 | 0 |
| G5. 30 min WIT | 6 | 844 ± 135 | 96.7 ± 0.4 | 2.9 ± 0.3 | 0.4 ± 0.1 | 0 |
| G6. HMP-30 min WIT | 7 | 621 ± 130 | 95.4 ± 1.1 | 4.2 ± 1.0 | 0.5 ± 0.2 | 0 |

Total islet count represents the number of individual islets with a diameter greater than 50 μm.

Perfusion of pancreata from large adult porcine donors (more than 2 years old and over 400 lb) may also be performed using the LifePort® transporter. In order to accommodate a tissue from a donor with higher organ resistance, such as adult porcine donors, the following adjustment may be made to the LifePort® transporter: (i) higher perfusion pressure values may be set to balance higher organ resistance and increased vasculature (by design, the transporter can regulate the infusion pressure between 10 and 65 mmHg), (ii) the cradle may be removed from the organ cassette to allow for the entire donor tissue, such as the pancreas, immersion in the cold perfusate, for proper temperature control, and/or (iii) pancreas lobular perfusion (i.e., head, tail, etc, can be separated and individually perfused) may be employed. Straight cannulation (discussed below) of the main vessels of the selected pancreas segment may be considered for lobular perfusion.

Figure 9:
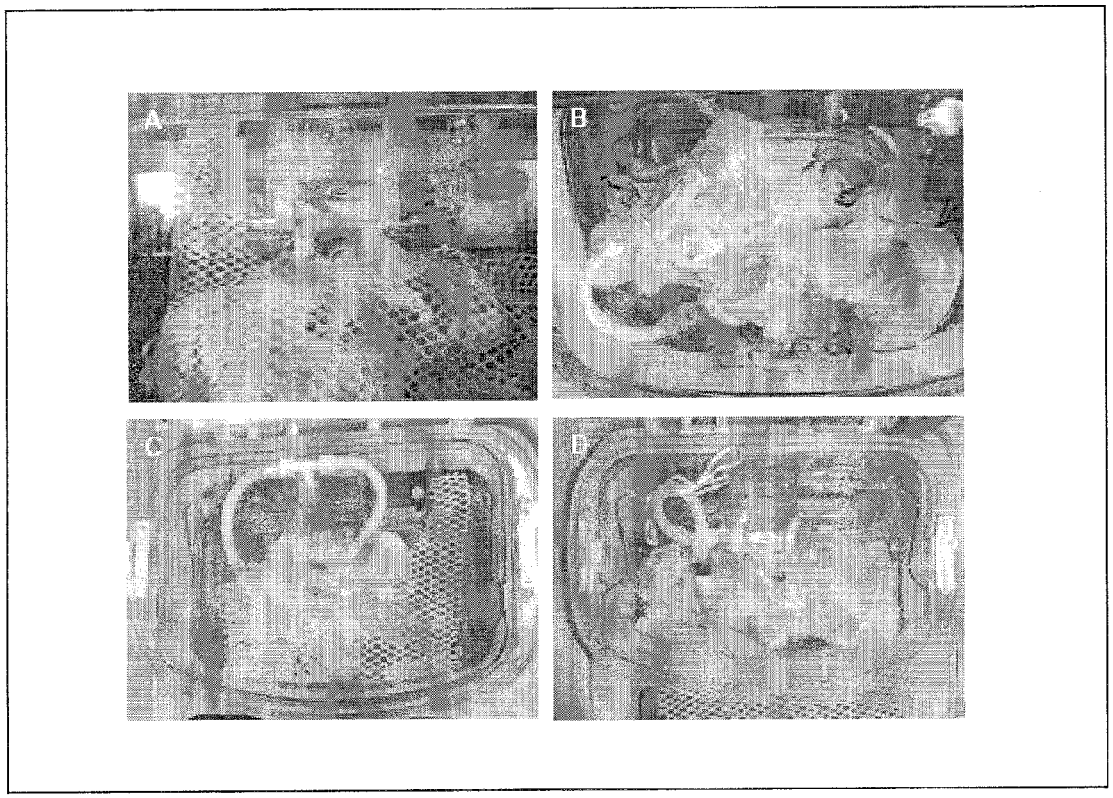
FIGS. 9A-D are photographs depicting variations in the method of cannulation for pancreas perfusion on the Life- Port® Transporter; A. Exemplary method of cannulation for juvenile pig pancreas using the proprietary seal-ring cannula (LifeLine Scientific), which avoids the need to insert cannulas into the individual arteries by allowing perfusion via the openings of the CT and SMA on an aortic patch clamped inside the seal-ring cannula (see also FIG. 6); B. Dual seal-ring cannulas each supporting the openings of the SMA and CT on individual aortic patches and linked via a coupler, This arrangement is useful and necessary when the openings of these two main arteries are spaced too far apart to be accommodated in a single seal-ring cannula; C. Straight cannulation of a large pig pancreas, or pancreatic lobe using insertion cannulas coupled together via a "T" connector for linking with the infusion port; D. A combination of a seal-ring cannula on one artery linked to a straight insertion cannula on the other artery, this configuration can be used as variant of the arrangement in B for larger pig pancreases or those in which the openings are anatomically too far apart for a single seal-ring cannula to be used.

In embodiments, lobular perfusion is an alternative option to whole donor tissue perfusion when the donor tissue or organ size exceeds cassette volume. For example, with respect to the pancreas, following recovery from the body and cleaning, the pancreas lobes are identified and visually delimited from the surrounding tissue. Ferrer et al. have recently documented in great details the anatomy of the pig pancreas and the variations in its vascular and ductal configuration (Ferrer J., Scott W. E., III, Weegman B. P. et al., Pig pancreas anatomy: implications for pancreas procurement, preservation, and islet isolation. Transplantation 2008, 86:1503-1510). For lobular perfusion, the major vessel(s) of each pancreas lobe/segment may be individually straight-cannulated (cannula inserted into the vessel lumen). If more than one cannula is used, a coupler is employed to join all cannulae and to connect them to the infusion port as illustrated in FIG. 9. For example, the SMA, or its branch, and the splenic artery are recommended for machine perfusion of the pancreas tail using straight-cannulation.

Figure 3:
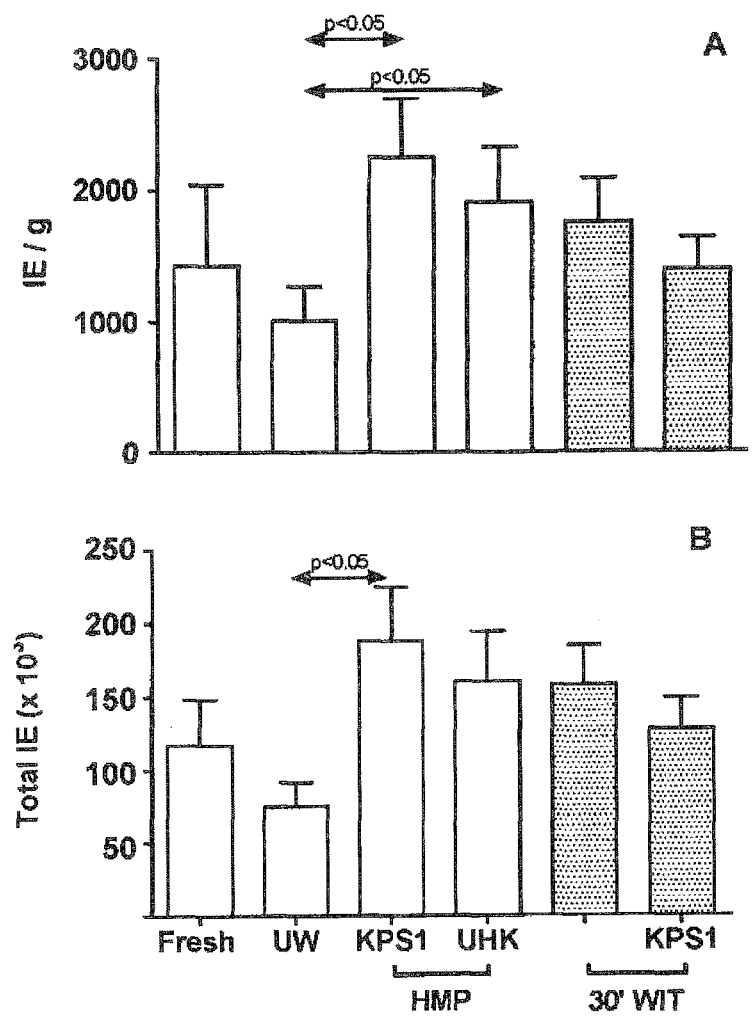
FIGS. 3A and B are graphical representations of islet yields expressed as both islet equivalents (IEQ) per gram of pancreas (A) and total IEQ (B) where the data for each group are expressed as the mean (±SEM)
Figure 4:
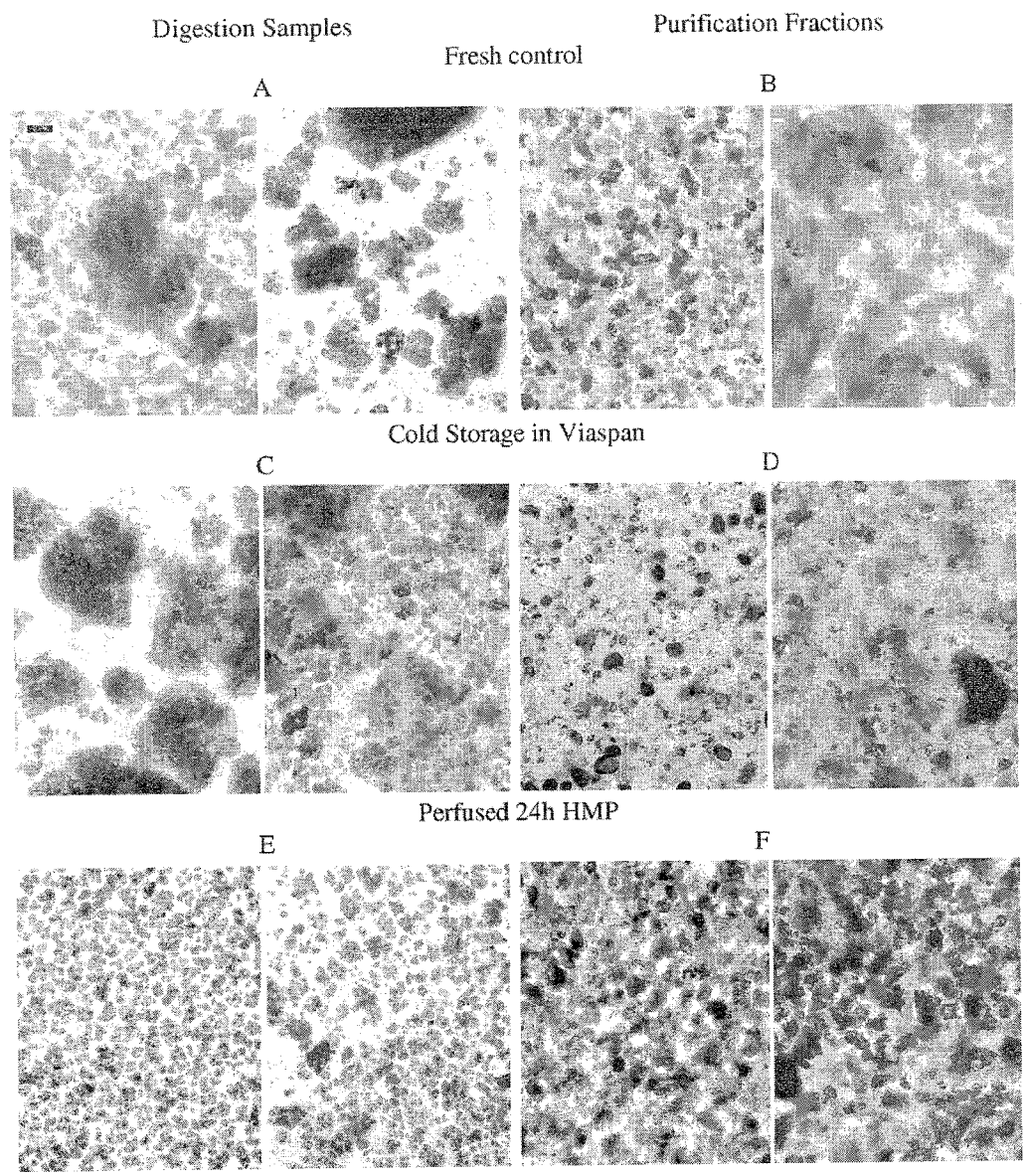
FIGS. 4A-F depict light micrographs (100× magnification) showing the relative purity of the respective islet preparations at the end of the digestion phase (A, C, E) and after density gradient purification (B, D, F), all panels are shown at the same magnification and represented by the 100 μm scale bar shown in the top left hand corner.

The effect of prior warm ischemia on islet yield is also shown in FIG. 3. Islet retrieval from young porcine pancreases was not compromised after 30 min of warm ischemia (G5) and was further maintained after an additional 24 h of hypothermic machine perfusion (G6). Islet Integrity Table 3 summarizes the data for islet function in terms of insulin content and the ability to respond to respond to a secretory glucose challenge. The latter is expressed as the Stimulation Index determined by comparing the insulin released during sequential exposure to a low (nonstimulatory, 2 mM) and high (stimulatory, 20 mM) concentration of glucose. The mean insulin content of islets isolated from perfused pancreata was significantly higher than that of the UV-Viaspan cold stored control group and was not significantly different to the mean values from fresh tissue. Moreover, the stimulation indices showed that the insulin secretory function of the islets isolated from perfused pancreata was not compromised when compared with the control groups even after 30 min prior warm ischemia. Ischemia alone, without subsequent perfusion, produced greater variability in the secretory function (G5) compared with all of the other groups as reflected in the standard error that was an order of magnitude greater. However, the imposition of HMP after 30 min WIT (G6) appeared to stabilize this response and insulin secretory function was not significantly different to controls. The energy status of the isolated islets, in terms of ATP content, was also preserved during the 24-h perfusion technique.

Figure 5:
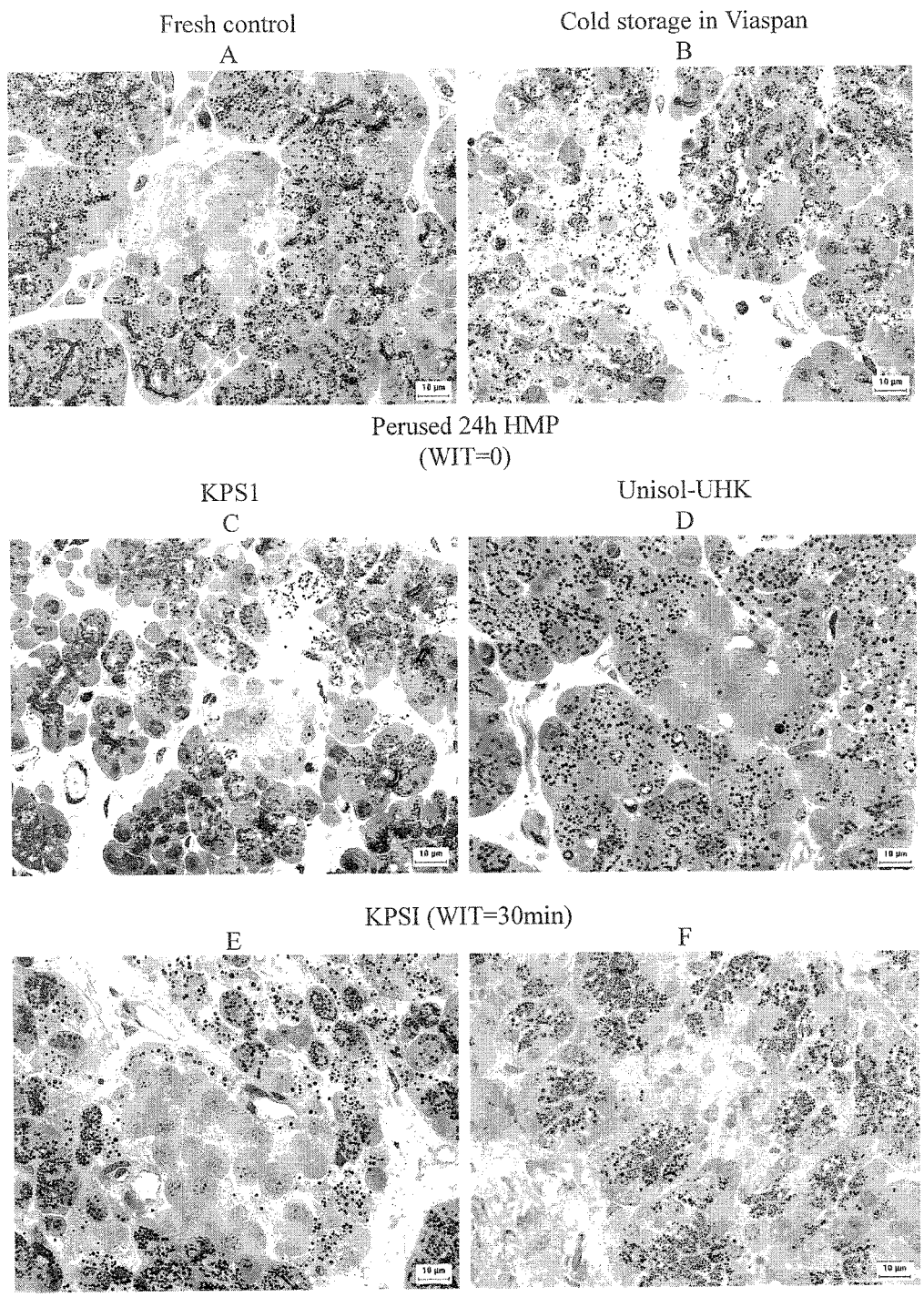
FIGS. 5A-F illustrate the histology of pancreatic biopsies sampled for each of the treatment groups: (A) Fresh control pancreas; (B) 24 h cold storage in UV-Viaspan; (C) 24 h HMP perfused with KPS1 (WIT=0); (D) 24 h HMP perfused with UNISOL UHK (WIT=0); (E) 24 h perfused with KPS1 (WIT=30 min); (F) 24 h HMP perfused with KPS1 (WIT=30 min). Scale bars: 10 μm.

Histological integrity of the pancreases was evaluated from wedge biopsies taken at the end of the preservation interval and examples from the control and experimental groups are shown in FIG. 5. FIG. 5A shows the typical morphology of fresh tissue with an intact islet, which stains more lightly with toluidine blue than the surrounding acini that are characterized by the abundance of zymogen granules. In marked contrast, tissue stored for 24 h in UV-Viaspan shows some degenerative changes characteristic of ischemic injury (FIG. 5B). These include budding, rounding, and vacuolated cells. Breakdown of the acini is also apparent with separation of cells and degranulation. Comparable micrographs prepared from pancreases perfused for 24 h with KPS1 or UNISOL-UHK are shown in FIGS. 5C and D, respectively. FIG. 5C shows an intact islet surrounded by acinar tissue that clearly shows changes in the acini compared with fresh tissue (FIG. 5A). The exocrine cells of the acini appear to have a looser structure consistent with the moderate edema that developed during perfusion. FIG. 5D shows an islet in pancreas perfused with UNISOL-UHK having intact morphology surrounded by acinar tissue. In this specimen the exocrine tissue appears better preserved with less disruption than that detected in either the 24-h cold storage group (FIG. 5B) or the group perfused with KPS1 (FIG. 5C). FIGS. 5E and F illustrates the morphology of islets and acinar tissue in sections of pancreas perfused for 24 h with KPS1 after 30 min prior warm ischemia. Again some acinar disruption is apparent consistent with both tissue edema and warm ischemic changes, but the islets have an intact morphology comparable with those from islets subjected to hypothermic perfusion without prior warm ischemia.

Islet stimulation indices were equivalent between the groups and similar to controls (G1). Insulin content (ng/ml/IEQ) was different between the treatment groups with the highest insulin content in islets harvested from HMP pancreata. Dithizone staining for islets consistently showed more uniform digestion of the perfused organs, with greater separation of the tissue, less entrapped islets, and higher islet yield and purity. The salutary effects of HMP for 24 h were also manifest after 30-min prior warm ischemia. We conclude that 24 h of HMP is well tolerated, leading to moderate edema but no loss of function of the harvested islets. The edema appears to aid in enzymatic digestion, producing a greater yield and purity of islets compared with pancreas subjected to 24 h of static cold storage.

Figure 7:
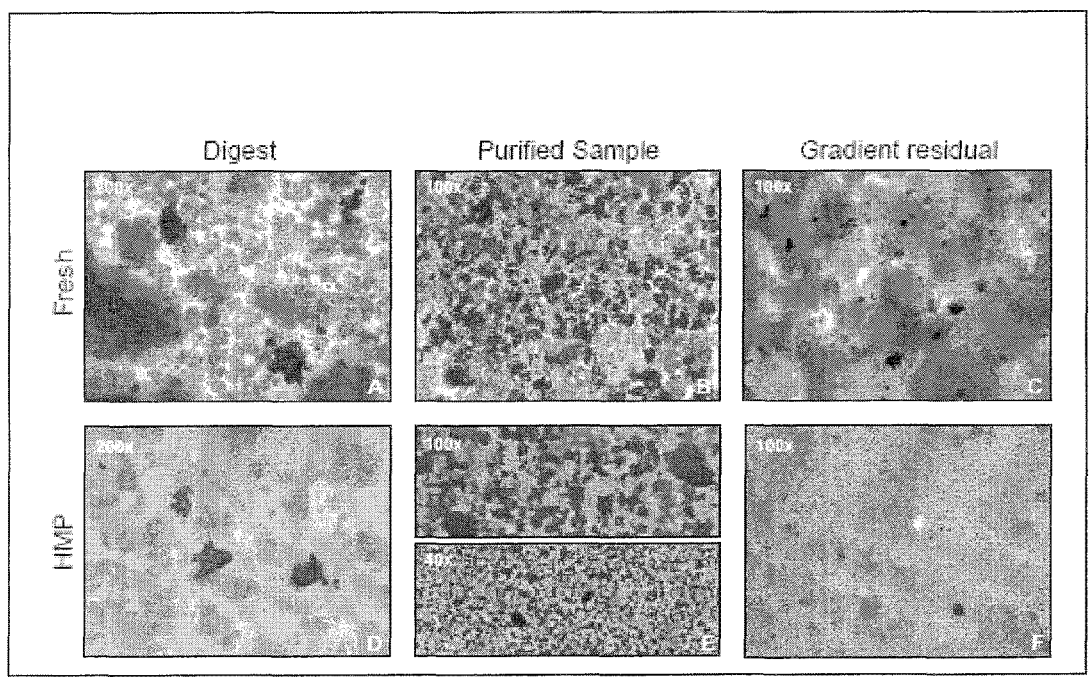
FIGS. 7A-F are light micrographs illustrating the effect of HMP on subsequent islet isolation at various magnifications, as indicated, showing the presence of isolated islets at different stages in the processing of both Fresh (panels A-C) and HMP pancreases (panels D-F); islets are identified by dithizone staining and appear purple-red in contrast to the unstained exocrine tissue which appears grey-brown; the pancreatic digest stained during the enzymatic processing shows a typically more uniform digest and isolated cleaved islets in the perfused pancreas (D) compared with the more non-homogeneous digest observed using freshly isolated pancreas (A); the more homogeneous digest typically derived using perfused pancreases often resulted in a cleaner separation of isolated islets on the density gradient yielding a more highly purified preparation of islets (E) compared with the either fresh (B) or statically cold stored pancreas (not shown); this differential separation during gradient purification was also manifest in examination of the gradient residual, which in the case of fresh pancreas often included many trapped or embedded islets (C) compared with perfused pancreases which showed a "clean" residual fraction with very few identifiable islets (F); this apparent differential effect on islet separation and purification was also manifest in the yield of islets obtained as an end-product (see data in Table 5, below)

Juvenile pig pancreata recovered, cannulated and perfused using the aforementioned methods are successfully preserved for up to 24 hour on the LifePort® transporter. As shown in Table 5, prolonged hypothermic perfusion results in uniform fluid accumulation within the organ (136±12%, n=19) even at low perfusion pressure (10 mmHg). The edema proves to be advantageous for islet isolation. It provides a disrupted extracellular space that helps free rapidly more islets during subsequent enzymatic digestion and generates a more homogeneous digest, with less mantled and entrapped islets, in comparison to fresh and static stored pancreata (see FIG. 7 and Table 5). The hypothermic perfusion also preserves islet function and viability (Table 5).

TABLE 5

Islet Yield and Function Indices

| PANCREAS/ISLET CHARACTERISTICS | FRESH (untreated control) [N = 10] | SCS (Viaspan) [N = 9] | HMP* [N = 19] |
|---|---|---|---|
| Pancreas Weight (g) | 112 ± 6 | 118 ± 5 | 101 ± 2 |
| Post-preservation edema (%) | — | −2.8 ± 0.7 | 136 ± 12 |
| Total islet yield (IEQ × 1000) | 147 ± 31 | 75 ± 16 | 165 ± 20* |
| Insulin Stimulation Index | 5.8 ± 1.1* | 2.5 ± 0.4 | 3.8 ± 0.5* |
| High-glucose insulin [ng/mL/IEQ] | 0.27 ± 0.1 | 0.20 ± 0.05 | 0.25 ± 0.04 |
| Insulin content [ng/mL/IEQ] | 9.35 ± 3.1 | 4.75 ± 1.00 | 9.92 ± 1.7* |

*$p < 0.05$ vs. Static Cold Storage Group (SCS)

Figure 10:
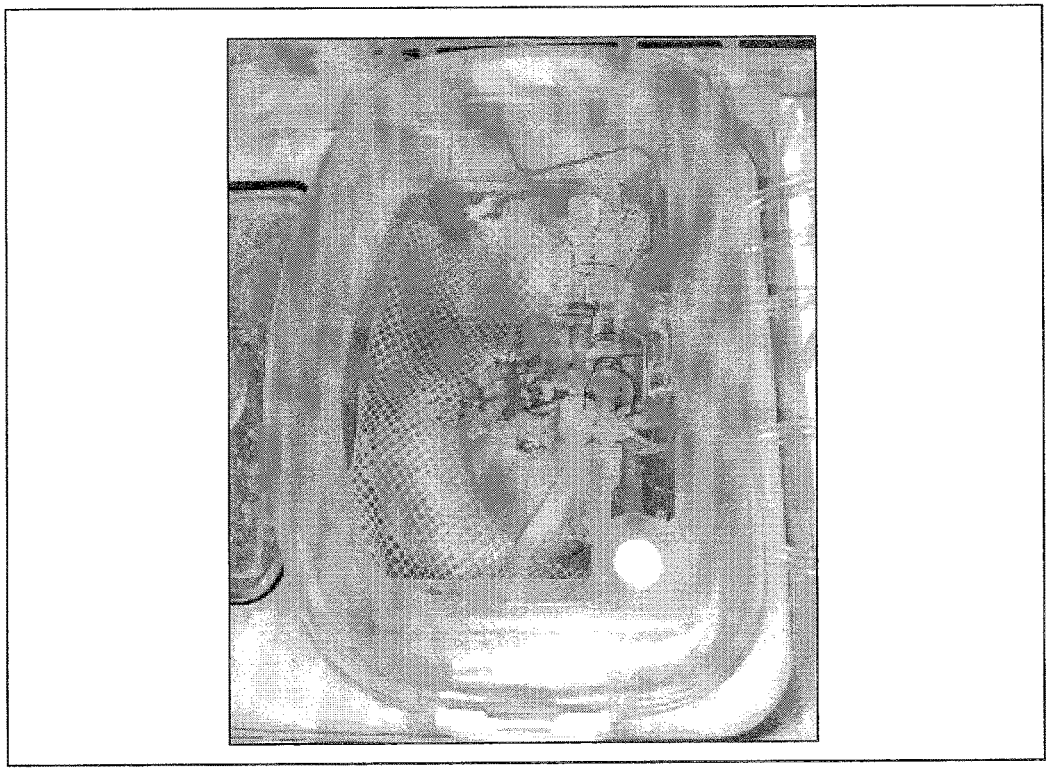
FIG. 10 is a photograph depicting hypothermic perfusion of human pancreas on the LifePort® transporter.
Figure 11:
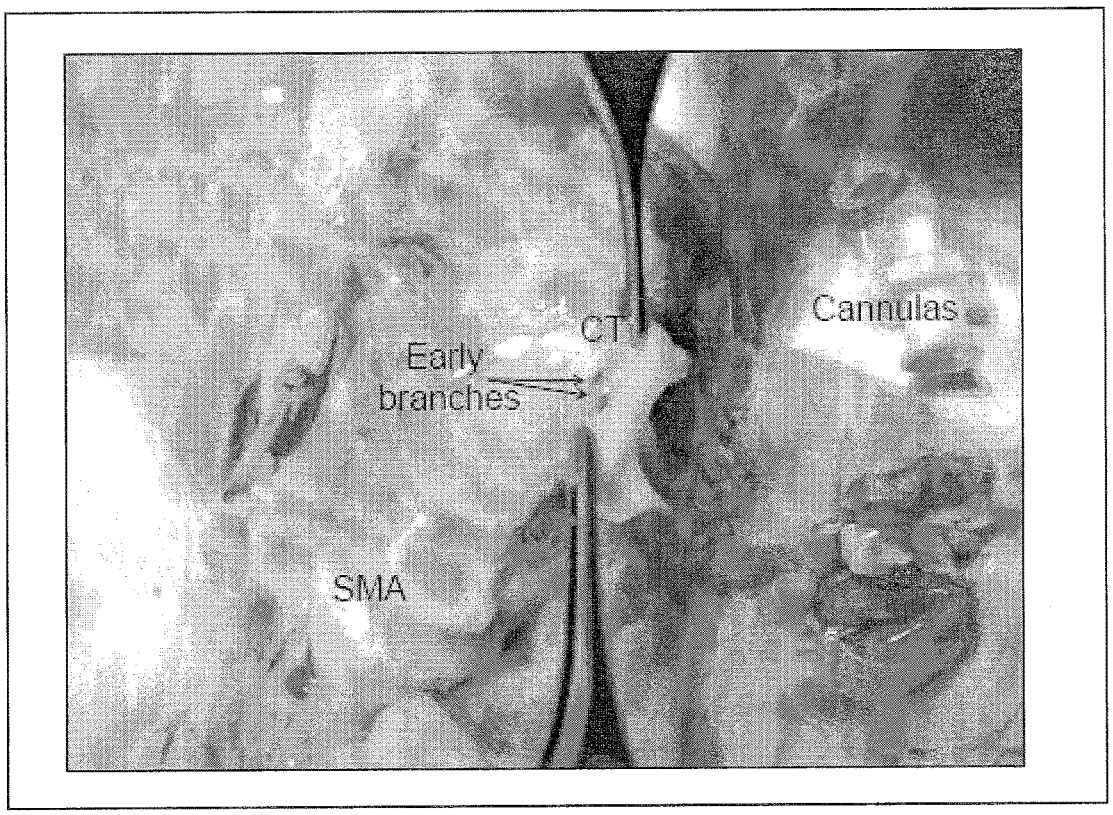
FIG. 11 is a photograph depicting a vascular cut-down to illustrate anatomical variants with early diverging side branches; successful perfusion of the pancreas, especially from young pigs, via the SMA and celiac trunk requires extreme care to avoid occlusion of early side branches by inserted cannulas such as those illustrated here. These anatomical constraints are prevalent in young pig pancreata as illustrated by the vessel cut-down shown here. The risk of undesirable occlusion of these side branches is avoided by use of a seal-ring cannula as described in the text and illustrated in FIG. 6.

Hypothermic perfusion of human pancreata may be performed following the steps of young pig whole pancreas perfusion method discussed above, with the exception of the cannulation site and cannula type. Under normal clinical recovery protocols, human pancreata are procured without the aortic patch, but with the duodenal segment attached and with intact vasculature. In this case the SMA and splenic artery are individually straight cannulated (as discussed below) and simultaneously perfused during pancreas machine preservation (FIG. 10). The transporter organ cassette without modification can accommodate the human pancreas. However, in comparison to the pig pancreas, the human pancreas may be highly fibrotic, which may need to be considered along with donor medical history for optimizing the perfusion pressure of the human pancreas.

What is claimed is:

1. A method of isolating a cellular product, comprising:
   providing a donor tissue having desired cells and undesired cells;
   connecting a perfusion apparatus to the donor tissue to allow fluid communication between the donor tissue and the perfusion apparatus;
   performing hypothermic machine perfusion by perfusing the donor tissue with a perfusion solution under hypothermic conditions, wherein an $O_2$ content in the perfusion solution is replenished during the perfusion, and the perfusion solution is a hypothermic blood substitute, comprising one or more members selected from the group consisting of cytoprotective agents and perfluorochemicals;
   developing edema during perfusion of the donor tissue to form a swelled tissue via increasing a first perfusion pressure applied by the perfusion apparatus to the tissue to achieve a second perfusion pressure, where the second perfusion pressure is in a range of from about 20 mmHg to about 50 mm Hg;
   treating the swelled tissue with a digestive enzyme;
   monitoring the extracellular space in the donor tissue by microdialysis; and
   separating the desired cells from undesired cellular material to obtain a cellular product; wherein the tissue is a pancreas, the oxygen consumption rate of the donor tissue is assessed before the perfusion apparatus is connected to the donor tissue and the oxygen consumption rate of the donor tissue is assessed and monitored after the perfusion apparatus is connected to the donor tissue, and an $O_2$ demand of the donor tissue is satisfied throughout a preservation interval/process occurring from the time the perfusion apparatus is connected to the donor tissue to a time when the perfusion apparatus is disconnected from the donor tissue.

2. The method of claim 1, further comprising:
   monitoring buoyancy of the donor tissue to assess the extent of edema;
   monitoring surface area of the donor tissue to assess the extent of edema;
   monitoring a circumference of the donor tissue to assess the extent of edema;
   monitoring mass of the donor tissue to assess the extent of edema; and/or
   monitoring volume of the donor tissue to assess the extent of edema.

3. The method of claim 1, wherein the swelled tissue has a mass that is at least 110% of an initial non-perfused mass of the donor tissue, and/or the swelled tissue has a volume that is at least 110% of an initial non-perfused volume of the donor tissue.

4. The method of claim 3, wherein the mass of the swelled tissue is from about 150% to about 250% of the mass of the donor tissue, and/or the volume of the swelled tissue is from about 150% to about 250% of the volume of the donor tissue.

5. The method of claim 1, wherein the swelled tissue has a mass that is less than 300% of an initial non-perfused mass of the donor tissue, and/or the swelled tissue has a volume that is less than 300% of an initial non-perfused volume of the donor tissue.

6. The method of claim 1, further comprising slicing the pancreas.

7. The method of claim 1, wherein the tissue is pancreatic tissue and the cellular product comprises pancreatic islets.

8. The method of claim 1, further comprising introducing cytoprotective agents during perfusion of the donor tissue for preventing cold-induced cell death of the donor tissue.

9. The method of claim 1, further comprising introducing cytoprotective agents during perfusion of the donor tissue for preventing cells of a donor pancreas from entering destructive pathways.

10. The method of claim 1, further comprising introducing cytoprotective agents during perfusion of the donor tissue for inhibiting mitochondrial dysfunction in cells of a donor pancreas.

11. The method of claim 1, further comprising preventing anaerobic glycolysis in the donor tissue.

12. The method of claim 11, wherein preventing anaerobic glycolysis in the donor tissue comprises introducing perfluorochemicals into the perfusion solution.

13. The method of claim 1, further comprising preventing oxygen deprivation/depletion in the donor tissue.

14. The method of claim 13, wherein preventing oxygen deprivation/depletion in the donor tissue comprises introducing perfluorochemicals into the perfusion solution.

15. The method of claim 1, further comprising disconnecting the perfusion apparatus from the donor tissue.

16. The method of claim 1, further comprising replenishing $O_2$ content in the perfusion solution during perfusion.

17. The method of claim 1, wherein the donor tissue is from a heart-beating donor.

18. The method of claim 1, wherein the donor tissue is from a non-heart-beating donor.

19. The method of claim 1, wherein monitoring the extracellular space in the donor tissue by microdialysis comprises implanting a dialysis probe into the donor tissue and assessing the concentration of interstitial fluid components.

20. The method of claim 19, wherein the concentration of interstitial fluid components is assessed periodically.

21. The method of claim 19, wherein the interstitial fluid components are selected from the group consisting of glucose, lactate, pyruvate, glycerol, ATP, $O_2$ and $CO_2$.

22. The method of claim 1, wherein the donor tissue is from a mammal.

23. The method of claim 22, wherein the mammal is a human.

24. The method of claim 22, wherein the mammal is a pig.

25. The method of claim 1, wherein the hypothermic machine perfusion is performed with a perfusion solution that is at a temperature of 5-7° C.

26. The method of claim 19, wherein the dialysis probe comprises a semi-permeable bio-compatible membrane as an active part.

27. A method of isolating a cellular product, comprising:
providing a donor tissue having desired cells and undesired cells;
connecting a perfusion apparatus to the donor tissue to allow fluid communication between the donor tissue and the perfusion apparatus;
performing hypothermic machine perfusion by perfusing the donor tissue with a perfusion solution under hypothermic conditions, wherein
an $O_2$ content in the perfusion solution is replenished during the perfusion,
ATP levels in the donor tissue is increased during perfusion, and
the perfusion solution is a hypothermic blood substitute, comprising: cytoprotective agents and perfluorochemicals;
developing edema during perfusion of the donor tissue to form a swelled tissue, wherein developing edema during perfusion of the donor tissue comprises:
increasing a first flow rate of the perfusion solution through the tissue to achieve a second flow rate, where the second flow rate is in the range of from about 20 ml/min to about 30 ml/min;
treating the swelled tissue with a digestive enzyme;
monitoring the extracellular space in the donor tissue by microdialysis; and
separating the desired cells from undesired cellular material to obtain a cellular product; wherein
the tissue is a pancreas,
the oxygen consumption rate of the donor tissue is assessed before the perfusion apparatus is connected to the donor tissue and the oxygen consumption rate of the donor tissue is assessed and monitored after the perfusion apparatus is connected to the donor tissue, and
an $O_2$ demand of the donor tissue is satisfied throughout a preservation interval/process occurring from the time the perfusion apparatus is connected to the donor tissue to a time when the perfusion apparatus is disconnected from the donor tissue.

* * * * *